United States Patent
Tabuchi et al.

(10) Patent No.: US 10,702,455 B2
(45) Date of Patent: Jul. 7, 2020

(54) GEL COMPOSITION, SHEET, AND PRODUCTION METHOD THEREFOR

(71) Applicant: DSP Gokyo Food & Chemical Co., Ltd., Osaka (JP)

(72) Inventors: Akira Tabuchi, Osaka (JP); Hiroshi Egawa, Osaka (JP); Yohei Baba, Osaka (JP)

(73) Assignee: DSP Gokyo Food & Chemical Co., Ltd., Osaka (JP)

( * ) Notice: Subject to any disclaimer, the term of this patent is extended or adjusted under 35 U.S.C. 154(b) by 0 days.

(21) Appl. No.: 16/311,385

(22) PCT Filed: Jun. 24, 2016

(86) PCT No.: PCT/JP2016/068890
§ 371 (c)(1),
(2) Date: Dec. 19, 2018

(87) PCT Pub. No.: WO2017/221415
PCT Pub. Date: Dec. 28, 2017

(65) Prior Publication Data
US 2019/0183746 A1    Jun. 20, 2019

(51) Int. Cl.
| | | |
|---|---|---|
| A61K 8/04 | (2006.01) | |
| A61K 8/73 | (2006.01) | |
| A61K 8/19 | (2006.01) | |
| C08L 5/00 | (2006.01) | |
| A61Q 19/00 | (2006.01) | |
| B01J 13/00 | (2006.01) | |
| A61K 8/02 | (2006.01) | |
| C08K 3/00 | (2018.01) | |
| A61K 8/26 | (2006.01) | |
| C08J 5/18 | (2006.01) | |

(52) U.S. Cl.
CPC ............... *A61K 8/042* (2013.01); *A61K 8/02* (2013.01); *A61K 8/0208* (2013.01); *A61K 8/0212* (2013.01); *A61K 8/19* (2013.01); *A61K 8/26* (2013.01); *A61K 8/73* (2013.01); *A61Q 19/00* (2013.01); *B01J 13/00* (2013.01); *B01J 13/0065* (2013.01); *B01J 13/0069* (2013.01); *C08J 5/18* (2013.01); *C08K 3/00* (2013.01); *C08L 5/00* (2013.01); *C08J 2305/00* (2013.01)

(58) Field of Classification Search
None
See application file for complete search history.

(56) References Cited

U.S. PATENT DOCUMENTS 6,245,354 B1 *  6/2001  Miyazaki ............... A61K 9/02
                                                    424/400
8,501,210 B2    8/2013  Fujisawa et al.

FOREIGN PATENT DOCUMENTS

| | | |
|---|---|---|
| EP | 2008643 A1 | 12/2008 |
| JP | 06181704 A | 7/1994 |
| JP | 08283305 A | 10/1996 |
| JP | 09248143 A | 9/1997 |
| JP | 10167951 A | 6/1998 |
| JP | 11332474 A | 12/1999 |
| JP | 2000354460 A | * 12/2000 |
| JP | 2001252032 A | 9/2001 |
| JP | 2004180549 A | 7/2004 |
| JP | 2004201606 | * 7/2004 |
| JP | 2004201606 A | 7/2004 |
| JP | 2007238538 A | 9/2007 |
| JP | 2009060794 A | 3/2009 |
| JP | 2012012328 A | 1/2012 |
| JP | 2016121279 A | 7/2016 |
| WO | 9729777 A1 | 8/1997 |
| WO | 0044242 A1 | 8/2000 |
| WO | 2007136083 A1 | 10/2009 |

OTHER PUBLICATIONS

International Preliminary Report on Patentability and Written Opinion for International Application No. PCT/JP2016/068890, dated Dec. 25, 2018, with translation—10 pages.
International Search Report issued in PCT/JP2016/068890, dated Aug. 2, 2016, 5 pages.
Extended European Search Report for European Application No. 16 906 333.6, dated Jan. 14, 2020, 10 pages.
International Preliminary Report on Patentability and Written Opinion for International Application No. PCT/JP2016/068891, dated Dec. 25, 2018, with translation, 11 pages.
Ravachol, J., et al., "Mechanisms involved in xyloglucan catabolism by the cellulosome-producing bacterium Ruminiclostridium cellulolyticum," Mar. 7, 2016, pp. 1-17, vol. 6, No. 1, XP055476503, Scientific Reports.
Extended European Search Report for European Application No. 16 906 332.8, dated Dec. 4, 2019, 12 pages.
USPTO Non-Final Office Action issued in U.S. Appl. No. 16/311,408, dated Feb. 10, 2020, 25 pages.

* cited by examiner

*Primary Examiner* — Robert A Wax
*Assistant Examiner* — Melissa S Mercier
(74) *Attorney, Agent, or Firm* — RatnerPrestia

(57) ABSTRACT

Provided is a gel composition including a partial degradation product of the galactose moiety of galactoxyloglucan, a compound that is a mixture of one kind or two or more kinds selected from magnesium salt, calcium salt, aluminum salt, and sodium salt, and an aqueous solvent.

11 Claims, No Drawings

GEL COMPOSITION, SHEET, AND PRODUCTION METHOD THEREFOR

CROSS REFERENCE TO RELATED APPLICATION

This application is the U.S. National Phase Application of PCT/JP2016/068890, filed Jun. 24, 2016, the contents of such application being incorporated by reference herein.

FIELD

The present invention relates to a gel composition, sheet, and production method therefor.

BACKGROUND

Conventionally, galactoxyloglucan is used as a natural polysaccharide. Galactoxyloglucan includes glucose, xylose, and galactose as constituent sugars, a main chain of which has β-1,4-bonded glucose, and a side chain of which has xylose and galactose bonded to the xylose. Galactoxyloglucan itself is not usually gelled.

Meanwhile, LM pectin is also used as a natural polysaccharide, and, in a solution with LM pectin dissolved in water, when calcium ions are added thereto, carboxy groups are crosslinked with the calcium ions and thereby LM pectin is gelled.

Contrarily, since galactoxyloglucan is a neutral polysaccharide, it is not gelled even if ions such as calcium are added thereto.

Meanwhile, there has been proposed a partial degradation product of the galactose moiety of galactoxyloglucan, which is obtained by partially degrading (partial degradation) to remove a galactose moiety constituting a part of the side chain of galactoxyloglucan using refined β-galactosidase derived from microorganisms (hereinafter also referred to simply as "galactose-partial degradation product" or "partial degradation product") (see Patent Literatures 1 and 2). When galactose-partial degradation product is mixed with an aqueous solvent, a mixture thereof shows a thermal behavior having a reversed relationship with the thermal behavior of the galactoxyloglucan. Specifically, the galactose-partial degradation product is gelled when heated and solated when cooled so that it shows a thermal behavior in this sol/gel change is reversible. Such a thermal behavior is called reverse thermal gelation characteristics. The galactose-partial degradation product is derived from natural polysaccharides and is not subjected to chemical modification (addition), and therefore is harmless to humans and the environment. Therefore, gel compositions produced using the galactose-partial degradation product can be widely used in foods, cosmetics, pharmaceutical formulations and the like. There have been proposed, as a production method for a gel composition including a galactose-partial degradation product of this kind, a method for producing a gel composition by mixing a cooled aqueous solvent with a galactose-partial degradation product to allow the galactose-partial degradation product to dissolve in the aqueous solvent, and gelling the dissolved solution by heating, and a method for producing a film composition by promoting drying of the produced gel (see Patent Literatures 1 and 2).

CITATION LIST

Patent Literature

Patent Literature 1: JP H8-283305
Patent Literature 2: International Publication WO97/29777

SUMMARY

Technical Problem

However, it is hard to say that the gel compositions mentioned in Patent Literatures 1 and 2 have sufficient elasticity and strength.

Further, although it is conceivable to produce a sheet with a reduced water content by drying these gel compositions, only a sheet having insufficient flexibility and strength is produced when these gel compositions are dried.

In general, it is said that an aqueous solvent is preferably mixed with polysaccharides in order to prevent formation of undissolved lumps at the time of contact of the aqueous solvent with the polysaccharides, in order to easily produce a gel composition including polysaccharides. This is because a powdery solid matter (nonhydrate product) resulting from nonhydrated polysaccharides remains in the produced gel composition, which causes deterioration in quality. Also, a long time and much labor are needed to dissolve polysaccharides which have become undissolved lumps by completely hydrating deep inside the polysaccharides.

In this regard, according to the methods of Patent Literatures 1 and 2, it is disclosed that, when producing a gel composition using a galactose-partial degradation product, the galactose-partial degradation product is mixed with a cooled aqueous solvent to allow themselves to be dissolved. However, these methods necessitate cooling an aqueous solvent followed by mixing of the galactose-partial degradation product, which takes a lot of time and labor for preparation. These methods also cause excessive viscosity of the mixture, which may cause a difficulty in handling when it is transferred to a desirable container and is gelled by heating. Also, these methods may cause a difficulty in filling a desirable container with a sufficient amount of the mixture or cause air bubbles to be easily entrained in the mixture during preparation or filling of a solution. Thus, it is hard to say that a gel composition can be easily produced by these methods of Patent Literatures 1 and 2.

Also, as mentioned above, only the sheet having insufficient flexibility and strength can be produced even by drying the gel composition produced by the methods of Patent Literatures 1 and 2.

In view of the above circumstances, it is an object of the present invention to provide a gel composition that is more excellent in elasticity and strength than heretofore, a sheet that is more excellent in flexibility and strength than heretofore, a production method that is capable of easily producing the gel composition, and a production method that is capable of easily producing the sheet.

Solution to Problem

As a result of diligent studies in order to achieve the aforementioned object, the inventors of the present application have found the following. Specifically, as mentioned above, it has been found that a gel composition, which is produced by dissolving a galactose-partial degradation product alone in water, has poor elasticity, and poor strength such as pull resistance.

Also, it has been found that a sheet, which is produced by drying the gel composition, has poor flexibility, and poor strength such as pull resistance.

As a result of the diligent studies based on these findings, the inventors of the present application have found that, by producing a gel composition with a certain composition additionally used with a galactose-partial degradation product, it is possible to produce a gel composition with more excellent in elasticity and strength than the case where such a composition is not additionally used. As a result, they have completed the gel composition of the present invention.

Also, as a result of the diligent studies on the production method for gel compositions based on the disclosed contents of Patent Literatures 1 and 2, the inventors of the present application have found the following. That is, it is generally known that, when a polysaccharide is mixed with an aqueous solvent, water in the aqueous solvent causes the polysaccharide to first hydrate and swell, and when the hydration and swelling further proceeds, it dissolves. As a result of taking into account this fact and the methods of Patent Literatures 1 and 2, it has been found that, since the methods of Patent Literatures 1 and 2 include a step of dissolving a galactose-partial degradation product by being mixed with a cooled aqueous solvent, the dissolved solution has a relatively high viscosity, which results in difficulty in handling of the dissolved solution. Also, as the temperature of the aqueous solvent is lowered by cooling, the time required for the galactose-partial degradation product to come into the hydration and swollen state, further the time required for it to convert from the hydration and swollen state into the dissolved state are shortened. Because of this, in the methods of Patent Literatures 1 and 2, viscosity develops at an early stage, and therefore, the dissolved solution must be forcibly stirred with a relatively strong force in order to homogeneously disperse the galactose-partial degradation product in the aqueous solvent. As a result of the diligent studies based on these findings, the inventors of the present application have found that, by mixing the aqueous solvent, the galactose-partial degradation product, and a compound that is one kind or a mixture of two or more kinds selected from the group consisting of magnesium salt, calcium salt, aluminum salt and sodium salt at room temperature, the galactose-partial degradation product can be dispersed in an aqueous solvent without occurrence of undissolved lumps in a mixture while the aforementioned compound is allowed to dissolve. Such mixing at room temperature causes the galactose-partial degradation product to be easily brought into a state where it is almost undissolved in the aqueous solvent, which results in producing a mixture having a low viscosity. Further, cooling or freezing the mixture having such a low viscosity causes the galactose-partial degradation product to be easily brought into a state where it is not dissolved but is easy to hydrate and swell to have a high viscosity, which results in producing a mixture having a high viscosity. Further, there is no need to cool the aqueous solvent in advance, by which time and labor for it is reduced or eliminated. It has also been found that, even if a mixture with the galactose-partial degradation product almost hydrated and swelled therein is heated, the mixture can be gelled and hence a gel composition can be produced. Further, it has been found that, even in the case where a galactose-partial degradation product and the aforementioned certain composition are concurrently used, a gel composition can be produced as well. Thus, the gel composition of the present invention and the production method for it have been achieved.

Further, it has been revealed that a sheet produced by drying the above gel composition is better in flexibility and strength than the sheets produced by drying gel compositions of Patent Literatures 1 and 2. Thus, it has been found that the sheet having such excellent properties can be produced only by drying the aforementioned gel composition, and hence the sheet of the present invention and the production method for it have been achieved.

Specifically, according to the present invention, there is provided a gel composition including a partial degradation product of the galactose moiety of galactoxyloglucan, a compound, and an aqueous solvent, wherein the compound is one kind or two or more kinds selected from the group consisting of magnesium salt, calcium salt, aluminum salt and sodium salt.

In the gel composition having the above construction, the compound is preferably two or more kinds selected from the group consisting of the magnesium salt, the calcium salt, the aluminum salt and the sodium salt.

In the gel composition having the above construction, the compound is preferably one kind or two or more kinds selected from the group consisting of the magnesium salt, the calcium salt and the aluminum salt.

In the gel composition having the above construction, the galactose-partial degradation product has 30 to 55% of a galactose moiety preferably degraded therein.

In the gel composition having the above construction, the content of the galactose-partial degradation product is preferably 1 to 5 mass % based on the total mass of the gel composition.

In the gel composition having the above construction, the content of the compound is preferably 0.1 to 12 mass % based on the total mass of the gel composition.

The gel composition having the above construction is used preferably for face pack.

According to the present invention, there is also provided a sheet, including a partial degradation product of the galactose moiety of galactoxyloglucan, an inorganic compound, and an aqueous solvent, wherein the inorganic compound is one kind or two or more kinds selected from the group consisting of magnesium salt, calcium salt and aluminum salt.

In the sheet having the above construction, the inorganic compound may include sodium salt or potassium salt.

In the sheet having the above construction, the water content of the sheet is preferably 10 to 35 mass % based on the total mass of the sheet.

The water content of the sheet herein means a ratio (percentage) of the decrement in mass of the sheet after drying relative to the mass of the sheet before drying, when the sheet is dried under a reduced pressure of −0.1 MPa (atmospheric pressure basis) at 70° C. for 8 to 12 hours.

In the sheet having the above construction, the content of the galactose-partial degradation product is preferably 15 to 80 mass % based on the total mass of the sheet.

In the sheet having the above construction, the content of the inorganic compound is preferably 10 to 70 mass % based on the total mass of the sheet.

According to the present invention, there is also provided a production method for a gel composition, including steps (1) to (3) mentioned below:

step (1) of mixing at room temperature a partial degradation product of the galactose moiety of galactoxyloglucan, a compound that is one kind or two or more kinds selected from the group consisting of magnesium salt, calcium salt, aluminum salt and sodium salt, and an aqueous solvent to obtain a mixture;

step (2) of cooling or freezing the mixture obtained in step (1); and step (3) of gelling the mixture cooled or frozen in step (2) by heating to obtain a gel composition that includes the galactose-partial degradation product, the compound, and the aqueous solvent.

The "room temperature" herein means a temperature within a range of from 15 to 35° C. "Mixing at room temperature" means mixing with the aqueous solvent being at room temperature. The state "cooled" means a state where the mixture of the aqueous solvent and the galactose-partial degradation product is not solidified by lowering the temperature, and also means the state where liquefied portions and solidified portions (i.e., frozen portions) are both present. The state "frozen" means a state where the mixture of the aqueous solvent and the galactose-partial degradation product is solidified by lowering the temperature.

Meanwhile, the "dispersed" state of the galactose-partial degradation product means a state where, while the aqueous solvent penetrates galactose-partial degradation product which is entirely in powder form, it is present in the aqueous solvent with little formation of a highly viscous (adhesive) layer on the surface layer. The state "hydrated and swollen" means a state where the galactose-partial degradation product which is entirely in powder form fully absorbs the aqueous solvent, and the galactose-partial degradation product as a whole is kept in a highly viscous state. The state "dissolved" means a state where polysaccharide molecule chains are detached from the highly viscous surface layer and disperse from the surface layer into the solvent. The state "undissolved lumps" means a state where the galactose-partial degradation product in powder form as a whole is lumped or such undissolved lumps are further form a group, resulting from that the galactose-partial degradation product in powder form which is in aggregated form (forming a aggregated product) comes into contact with water, allowing only the outer layer of the aggregated product having an air layer contained therein to form a highly viscous state by the contact with water, and thereby making the aqueous solvent less penetrate the inside of the aggregated product.

In step (1) of the production method for the gel composition having the above construction, the galactose-partial degradation product, the compound, and the aqueous solvent are preferably mixed at 18 to 30° C.

In step (1) of the production method for the gel composition having the above construction, it is preferable that the galactose-partial degradation product be mixed with the aqueous solvent and thereafter further mixed with the compound.

According to the present invention, there is also provided a production method for a sheet, including steps (1) to (4) mentioned below:

step (1) of mixing at room temperature a partial degradation product of the galactose moiety of galactoxyloglucan, an inorganic compound that is one kind or two or more kinds selected from the group consisting of magnesium salt, calcium salt and aluminum salt, and an aqueous solvent to obtain a mixture;

step (2) of cooling or freezing the mixture obtained in step (1);

step (3) of gelling the mixture cooled or frozen in step (2) by heating to obtain a gel composition that includes the galactose-partial degradation product, the inorganic compound, and the aqueous solvent; and step (4) of drying the gel composition produced in step (3) to produce a sheet.

The production method for the sheet having the above construction encompasses the production method which includes producing a gel composition by performing steps (1) to (3) of the above gel composition production method, using the inorganic compound(s) other than sodium salt among the compounds that is one kind or a mixture of two or more kinds selected from the group consisting of magnesium salt, calcium salt, aluminum salt and sodium salt, followed by subjecting the produced gel composition to the above step (4) to produce a sheet.

In the production method for the sheet having the above construction, the inorganic compound may further include sodium salt or potassium salt.

In step (1) of the production method for the sheet having the above construction, the galactose-partial degradation product, the inorganic compound, and the aqueous solvent are preferably mixed at 18 to 30° C.

In step (1) of the production method for the sheet having the above construction, it is preferable that the galactose-partial degradation product be mixed with the aqueous solvent and thereafter further mixed with the inorganic compound.

DESCRIPTION OF EMBODIMENTS

Hereinafter, embodiments of a gel composition, a sheet, and production methods therefor of the present invention will be described.

A gel composition of this embodiment includes a partial degradation product of the galactose moiety of galactoxyloglucan, a compound, and an aqueous solvent, wherein the compound is one kind or two or more kinds selected from the group consisting of magnesium salt, calcium salt, aluminum salt and sodium salt.

The partial degradation product of the galactose moiety of galactoxyloglucan means a substance, which is obtained by partially degrading to remove the galactose moiety on the side chain of galactoxyloglucan, and the partial degradation product of the galactose moiety of galactoxyloglucan hereinafter may be abbreviated as the galactose-partial degradation product. Galactoxyloglucan means galactoxyloglucan (complete galactoxyloglucan) of which the galactose moiety on the side chain is not removed by partial degradation with later-described enzyme treatment. This complete galactoxyloglucan may also be referred to as native galactoxyloglucan.

Galactoxyloglucan is a constituent of a cell wall (a primary wall) of a higher plant such as dicotyledon and monocotyledon, and exists as a storage polysaccharide of some plant seeds. Galactoxyloglucan includes glucose, xylose, and galactose as constituent sugars, a main chain of which has β-1,4-bonded glucose, and a side chain of which has xylose and galactose bonded to the xylose. Galactoxyloglucan itself is not usually gelled, while being gelled in the presence of saccharide, ion, or alcohol.

Galactoxyloglucan may be galactoxyloglucan derived from any plants and obtainable from, for example, seeds of tamarind, jatoba, and nasturtium, cereal such as soybean, mung bean, kidney bean, rice, and barley, or skin of fruits such as apple. A preferable one is galactoxyloglucan derived from leguminous-plants tamarind seed because of the easiest availability and the large content of galactoxyloglucan. A commercially available one can be employed as such galactoxyloglucan.

The galactose-partial degradation product used for the production method of this embodiment is produced by the following production methods, for example. Specifically, the galactoxyloglucan derived from tamarind seed is maintained at 55° C. and then adjusted to pH 6 with trisodium citrate, followed by addition of β-galactosidase thereto, to react at 50 to 55° C. for 16 hours, while being stirred. Subsequently, after the enzyme is deactivated by heating at 95° C. for 30 minutes, the obtained product is returned to room temperature, followed by addition of an equal volume of ethanol thereto, to be left standing for 1 hour. Precipitates which were obtained after being left standing are collected by way of suction filtration and dried with a ventilation dryer, and thereafter the precipitates are pulverized to thereby produce a galactose-partial degradation product.

β-galactosidase to be used may be any product derived from plants or microorganisms, but a preferable one is enzyme derived from microorganisms such as *Aspergillus oryzae* and *Bacillus circulans*, or enzyme present in a galactoxyloglucan-containing seed. A commercially available one can be employed as such a β-galactosidase.

In the enzyme reaction with this β-galactosidase, the galactose moiety on the side chain of the galactose-partial degradation product is partially removed with the progress of reaction, and when the galactose removal ratio reaches about 30%, the reaction solution is rapidly thickened in viscosity and gelled. When the galactose removal ratio is in the range of 30 to 55%, the galactose-partial degradation product has reverse thermal gelation characteristics, whereby it is gelled when heated and solated when cooled. The galactose-partial degradation product tends to be not gelled with the galactose removal ratio of less than 30%, while to form an excessively hard gel with the removal ratio over 55% (see Patent Literatures 1 and 2).

In consideration of this, it is preferable to use the aforementioned galactose-partial degradation product in which 30 to 55% of the galactose moiety is degraded. By setting the removal ratio within this range, it is possible to produce a gel composition that is not excessively hard, while allowing it to exhibit sufficient gelation characteristics by heating. This makes it easier to allow the galactose-partial degradation product to exhibit the reverse thermal gelation characteristics whereby it is fully gelled when heated and fully solated when cooled in a reversible manner. As a result, the produced gel composition in which 30 to 55% of a galactose moiety is degraded can exhibit sufficient elasticity and strength.

The aforementioned galactose-partial degradation product in which 30 to 55% of a galactose moiety is degraded is produced from galactoxyloglucan in which 30 to 55% of a galactose moiety is degraded as mentioned above. Galactoxyloglucan usually includes about 37% of a side-chain xylose and about 17% of a side-chain galactose (see Gidley et al., Carbohydrate Research), 214 (1991), pp. 219-314). Therefore, it is calculated that the galactose-partial degradation product in which 30 to 55% of a galactose moiety is degraded includes 39 to 41% of a side-chain xylose and 8 to 12% of a side-chain galactose. The ratio of degradation of a galactose moiety (that is, the galactose removal ratio) can be calculated by measuring an amount of galactoxyloglucan oligosaccharides generated by cellulase degradation of the obtained partial degradation product with high performance liquid chromatography (HPLC) (amino column).

Although the content of the galactose-partial degradation product is not particularly limited, but is preferably 1 to 10 mass % based on the total mass of the gel composition, more preferably 1 to 5 mass %, still more preferably 3 to 5 mass %.

With the content of the galactose-partial degradation product of 1 mass % or more, it is possible to more securely and sufficiently increase the strength of the gel composition. On the other hand, with the content of the galactose-partial degradation product of 10 mass % or less, it is possible to allow a moderate amount of an aqueous solvent to be retained in the gel composition to thereby allow the gel composition to exhibit a desired elasticity. Desired gel physical properties and texture can be also exhibited. Further, the gel composition can have sufficient flexibility and strength when formed into a sheet, for example, when the gel composition is formed into a sheet within a shallow (small depth) container (that is, in a state where the depth of the mixture is made small). When the concentration of the galactose-partial degradation product is low, water that could not contribute to gelation may form a layer on the upper side of the gel composition and the rest below it may form a gelled layer. In this case, the content of the galactose-partial degradation product is the content based on the total amount of the gelled layer below the water layer (separated water) after the water layer (separated water) is removed. That is, the content thereof is the content based on the total amount of the gel composition after concentrated.

The aforementioned compound, that is, a salt compound, is one kind or two or more kinds selected from the group consisting of magnesium salt, calcium salt, aluminum salt and sodium salt. Two or more kinds selected from this group may be a mixture thereof. The compound may be an organic compound, or may be an inorganic compound. Also, the aforementioned compound of two or more kinds includes a complex salt such as aluminum magnesium. When an inorganic compound of the compounds is used, a gel composition is produced by the production method for the gel composition of this embodiment so that a sheet can be produced using the obtained gel composition by a later-described production method for the sheet of this embodiment. On the other hand, when an organic compound of the compounds is used, a gel composition can be produced by the production method for the gel composition of this embodiment.

Chlorides of magnesium can be mentioned as the magnesium salt. That is, magnesium chloride ($MgCl_2$) can be mentioned as the magnesium salt. In addition, bromides of magnesium, silicate, sulfate, organic acid salt, organic ester salt, and the like can be mentioned as the magnesium salt. Gluconate, a pantothenate, acetate, and the like can be mentioned as the organic acid salt, and ascorbate phosphate, and the like can be mentioned as the organic ester salt.

Chlorides of calcium can be mentioned as the calcium salt. That is, calcium chloride ($CaCl_2$) can be mentioned as the calcium salt. In addition, bromides of calcium, silicate, sulfate, organic acid salt, organic ester salt, and the like can be mentioned as the calcium salt. Gluconate, pantothenate, acetate, and the like can be mentioned as the organic acid salt, and ascorbyl phosphate salt and the like can be mentioned as the organic ester salt.

Chlorides of aluminum can be mentioned as the aluminum salt. That is, aluminum chloride ($AlCl_3$) can be mentioned as the aluminum salt. In addition, bromides of aluminum, silicate, sulfate, organic acid salt, organic ester salt, and the like can be mentioned as the aluminum salt. Gluconate, pantothenate, acetate, and the like can be mentioned as the organic acid salt, and ascorbyl phosphate salt, and the like can be mentioned as the organic ester salt.

Chlorides of sodium can be mentioned as the sodium salt. That is, sodium chloride (NaCl) can be mentioned as the sodium salt. In addition, bromides of sodium, silicate, sulfate, organic acid salt, organic ester salt, and the like can be mentioned as the sodium salt. Gluconate, pantothenate, acetate, and the like can be mentioned as the organic acid salt, and ascorbyl phosphate salt and the like can be mentioned as the organic ester salt.

For these magnesium salt, calcium salt, aluminum salt, and sodium salt, those used as additives in pharmaceutical formulations may be employed. These compounds are preferably of such a grade as to be physiologically acceptable to be ordinarily and safely usable.

The aforementioned compounds each may be two or more kinds selected from the group consisting of magnesium salt, calcium salt, aluminum salt and sodium salt.

Among the compounds, magnesium salt, calcium salt, and a mixture thereof are preferable. When the compound is magnesium salt, calcium salt, or the mixture thereof, the gel composition can have further improved elasticity and strength.

Among the compounds, magnesium salt is particularly preferable, and specifically, magnesium chloride is particularly preferable.

The content of the compound is preferably 0.1 to 12 mass %, more preferably 1 to 6 mass % based on the total mass of the gel composition. When the content of the compound is 0.1 to 12 mass % based on the total mass of the gel composition, the elasticity and strength of the gel composition may be more satisfactorily exhibited.

The aqueous solvent is not particularly limited, provided that it is a solvent containing water; however, water, water containing a small amount of an organic solvent such as ethanol, and the like can be mentioned, for example. In this embodiment, the aqueous solvent in a state of aqueous solution, which is prepared by adding the aforementioned compound, other additives or the like to the aqueous solvent, can also be used. For example, when water is used as the aqueous solvent, water in a state of dilute salt aqueous solution, which is prepared by dissolving a small amount of an inorganic compound in water, can also be used. As the salt aqueous solution, sodium salt aqueous solution, calcium salt aqueous solution, buffer solution, and the like can be mentioned. As the buffer solution, a phosphate buffer solution, a citrate buffer solution, and the like of pH 4 to 7 can be mentioned.

The water content in the gel composition may be suitably set according to the intended use or the like, but is not particularly limited thereto, but is preferably above 35 mass %, more preferably 70 mass % or more based on the total mass of the gel composition. The water content of the gel composition herein means a ratio (percentage) of the decrement in mass of the gel composition after drying relative to the mass of the gel composition before drying, when the gel composition is dried under a reduced pressure of −0.1 MPa (atmospheric pressure basis) at 70° C. for 8 to 12 hours. Specifically, the water content of the gel composition means a value measured by the measuring method set forth in a later described example.

The gel composition of this embodiment may include additives other than the above, provided that the gel composition has excellent elasticity and strength. As the additives, for example, an oily substance can be mentioned, and olive oil, silicone oil, and the like can be mentioned as the oil substance.

The gel composition of this embodiment includes the galactose-partial degradation product and the compound to thereby have more excellent elasticity and strength than in the case where the compound is not included. Accordingly, the gel composition has more excellent elasticity and strength than ever.

As mentioned above, the gel composition of this embodiment includes a partial degradation product of the galactose moiety of galactoxyloglucan, a compound, and an aqueous solvent, wherein the compound is one kind or two or more kinds selected from the group consisting of magnesium salt, calcium salt, aluminum salt and sodium salt.

According to this construction, the gel composition has more excellent flexibility and strength by including the galactose-partial degradation product, the compound, and the aqueous solvent than in the case where the compound is not included.

In the gel composition of this embodiment, the compound is preferably two or more kinds selected from the group consisting of the magnesium salt, the calcium salt, the aluminum salt and the sodium salt.

In the gel composition of this embodiment, the compound is preferably one kind or two or more kinds selected from the group consisting of the magnesium salt, the calcium salt and the aluminum salt.

In the gel composition of this embodiment, 30 to 55% of a galactose moiety is preferably degraded in the galactose-partial degradation product.

According to this construction, the gel composition can sufficiently exhibit elasticity and strength by the removal of 30 to 55% of the galactose moiety.

In the gel composition of this embodiment, the content of the galactose-partial degradation product is preferably 1 to 5 mass % based on the total mass of the gel composition.

According to this construction, the gel composition in which the content of the galactose-partial degradation product is 1 to 5 mass % based on the total mass of the gel composition can sufficiently exhibit elasticity and strength.

In the gel composition of this embodiment, the content of the compound is preferably 0.1 to 12 mass % based on the total mass of the gel composition.

According to this construction, the gel composition in which the content of the compound is 0.1 to 12 mass % based on the total mass of the gel composition can sufficiently exhibit elasticity and strength.

The gel composition of this embodiment is used preferably for face pack.

With such construction, the gel composition is used for face pack so that the gel composition becomes more useful because the face pack has adhesiveness due to water contained in the gel structure, while retaining an active component inside the gel structure.

Next, a sheet of this embodiment obtained by using the gel composition will be described.

A sheet of this embodiment includes a partial degradation product of the galactose moiety of galactoxyloglucan, an inorganic compound, and an aqueous solvent, the inorganic compound being one kind or two or more kinds selected from the group consisting of magnesium salt, calcium salt and aluminum salt. Specifically, the sheet of this embodiment is formed by drying the gel composition of the aforementioned embodiment. That is, the sheet of this embodiment includes, as an inorganic compound, an inorganic anion salt compound among compounds (salt compounds) to be included in the aforementioned gel composition of this embodiment.

The water content of the sheet is not particularly limited. For example, it can be suitably set according to the thickness of the sheet or the like without particular limitation. The water content of the sheet is usually 10 mass % or more and 35 mass % or less, and preferably 10 mass % or more and 30 mass % or less, for example. This water content means a value measured by a method in a later-described example.

When the water amount of the sheet is 10 mass % or more and 35 mass % or less, the produced sheet has excellent flexibility, while having appropriate strength such as ductility. The sheet may have appropriate adhesiveness (tackiness). In this regard, the water content is more preferably 25 mass % or less. The water content can be adjusted or controlled by adjusting the content of the galactose-partial degradation product or the content of the inorganic compound in the gel composition, the thickness of the sheet, the drying temperature, the drying time, or the like.

The content of the galactose-partial degradation product is preferably 15 to 80 mass % and more preferably 15 to 70 mass % based on the total mass of the sheet. When the content of the galactose-partial degradation product is 15 to 80 mass % based on the total mass of the sheet, the sheet may more sufficiently exhibit flexibility and strength. Further, when it is 15 to 70 mass %, the sheet may much more sufficiently exhibit flexibility and strength.

Among the inorganic compounds, magnesium salt, calcium salt, and the mixture thereof are preferable. As the inorganic compound that is magnesium salt or calcium salt, those described above can be mentioned. When the inorganic compound is magnesium salt, calcium salt or the mixture thereof, the sheet can have further improved flexibility and strength.

Among the inorganic compounds, magnesium salt is particularly preferable, and specifically, magnesium chloride is more particularly preferable.

The inorganic compounds may further include sodium salt or potassium salt. As an inorganic compound of sodium salt, those described above can be mentioned. As an inorganic compound of potassium salt, chlorides of potassium can be mentioned. That is, as an inorganic compound of potassium salt, potassium chloride (KCl) can be mentioned.

The content of the inorganic compound is preferably 10 to 70 mass % based on the total mass of the sheet. When the content of the inorganic compound is 10 to 70 mass % based on the total mass of the sheet, the sheet may more sufficiently exhibit flexibility and strength.

The thickness of the sheet may be appropriately set according to the intended use or the like, but is not particularly limited thereto. For example, the thickness of the sheet may be 0.01 to 5 mm, preferably 0.03 to 3 mm, more preferably 0.1 to 1 mm, still more preferably 0.2 to 0.5 mm. When the thickness of the sheet is 0.03 to 3 mm, the sheet is hard to be broken and easy to be handled. Further, when the thickness of the sheet is 0.03 to 3 mm, pasting of the sheet can be easily made when it is required. The thickness of the sheet may be adjusted by adjusting the content of the galactose-partial degradation product or the content of the inorganic compound in the gel composition, or the thickness of the gel composition before drying.

The sheet preferably has extensibility, cracking resistance, pull resistance, adhesiveness (tackiness), shape retainability, water resistance, and heat resistance in addition to flexibility and strength.

The sheet of this embodiment includes a partial degradation product of the galactose moiety of galactoxyloglucan, the inorganic compound and an aqueous solvent to thereby have excellent elasticity and strength than ever.

As mentioned above, the sheet of this embodiment includes a partial degradation product of the galactose moiety of galactoxyloglucan, an inorganic compound and an aqueous solvent, and the inorganic compound is one kind or two or more kinds selected from the group consisting of magnesium salt, calcium salt and aluminum salt.

With such construction, the sheet includes the galactose-partial degradation product, the inorganic compound, and the aqueous solvent so that it has more excellent flexibility and strength than ever.

In the sheet of this embodiment, the inorganic compound may further include sodium salt or potassium salt.

In the sheet of this embodiment, the water content of the sheet is preferably 10 to 35 mass % based on the total mass of the sheet.

In the sheet of this embodiment, the content of the galactose-partial degradation product is preferably 15 to 80 mass % based on the total mass of the sheet.

With such construction, the content of the galactose-partial degradation product is 15 to 80 mass % based on the total mass of the sheet so that the sheet may more sufficiently exhibit flexibility and strength.

In the sheet of this embodiment, the content of the inorganic compound is preferably 10 to 70 mass % based on the total mass of the sheet.

With such construction, the content of the inorganic compound is 10 to 70 mass % based on the total mass of the sheet so that the sheet may more sufficiently exhibit flexibility and strength.

Next, a production method for the gel composition of this embodiment will be described.

The production method for the gel composition of this embodiment is not particularly limited, provided that a gel composition can be produced by dissolving a galactose-partial degradation product and the aforementioned compound in an aqueous solvent, for example, a method mentioned below is preferable.

The production method for the gel composition of this embodiment includes steps (1) to (3) mentioned below:

step (1) of mixing at room temperature a partial degradation product of the galactose moiety of galactoxyloglucan, a compound that is one kind or two or more kinds selected from the group consisting of magnesium salt, calcium salt, aluminum salt and sodium salt, and an aqueous solvent to obtain a mixture;

step (2) of cooling or freezing the mixture obtained in step (1); and step (3) of gelling the mixture cooled or frozen in step (2) by heating to obtain a gel composition that includes the galactose-partial degradation product and the compound.

In step (1) in the production method of this embodiment, the galactose-partial degradation product, the compound, and the aqueous solvent are mixed at room temperature to obtain a mixture thereof.

Dispersion liquid (i.e., suspension liquid) as a mixture in which the galactose-partial degradation product has been dispersed in the aqueous solvent can be obtained by mixing the galactose-partial degradation product with the aqueous solvent at room temperature. The aforementioned compound may be further mixed in this dispersion liquid thereafter. The aforementioned compound may be dissolved entirely or partially undissolved in the aqueous solvent.

As the temperature of the aqueous solvent is lowered by cooling, the time required for the galactose-partial degradation product to reach the hydration and swollen state and the time required for the galactose-partial degradation product to be transformed from the hydration and swollen state into the dissolved state are shortened. In such a state where the time required for the galactose-partial degradation product to reach the dissolved state is relatively short, a relatively strong stirring force is required in order to disperse the galactose-partial degradation product in the aqueous solvent as homogeneously as possible. That is, a relatively strong stirring force is required in order to dissolve the galactose-partial degradation product in the cooled aqueous solvent as homogeneously as possible.

On the other hand, the time required for the galactose-partial degradation product to reach the hydration and swollen state in the aqueous solvent at room temperature and the time required for the galactose-partial degradation product to reach the dissolved state are much longer than those in the case of using the cooled aqueous solvent, and therefore, the galactose-partial degradation product hardly dissolves even when the stirring is performed with the same force. Accordingly, the occurrence of undissolved lumps caused by the galactose-partial degradation product can be suppressed by mixing the galactose-partial degradation product with the aqueous solvent at room temperature in step (1).

Although the order in which the galactose-partial degradation product and the compound are added is not particularly limited, but it is preferable that the galactose-partial degradation product be mixed with the aqueous solvent, and thereafter the aforementioned compound be added thereto to be further mixed therewith. In this order in which the galactose-partial degradation product is mixed with the aqueous solvent and thereafter the aforementioned compound is further mixed therewith, the aforementioned compound can be mixed with them in a state where the galactose-partial degradation product is fully dispersed in the aqueous solution, so that the galactose-partial degradation product can be more homogeneously mixed therein. Thereby, the produced gel composition can easily exhibit elasticity and strength.

A gathered powder seems to occur in dispersion liquid during mixing of the galactose-partial degradation product with an aqueous solvent. However, this is not an undissolved lump and therefore the galactose-partial degradation product can be easily dispersed almost completely by lightly crumbling the gathering with spatula (spatel) or the like. The operation of "crumbling" herein means bringing a gathered substance back to the form or unit before it is gathered, and means an operation entirely different from stirring to be carried out generally for dissolving a substance.

The temperature of the aqueous solvent during mixing the aqueous solvent, the galactose-partial degradation product, and the aforementioned compound is not particularly limited, provided that it is at room temperature, but the temperature to be employed is preferably 18 to 30° C., more preferably 18 to 28° C. By mixing at 18° C. or higher, it is possible to disperse the galactose-partial degradation product in the aqueous solvent, while further avoiding occurrence of undissolved lumps. Thereby, it is possible to further suppress increase in viscosity caused, for example, when the galactose-partial degradation product has been dissolved. Also, the aforementioned compound can be easily dissolved in the aqueous solvent. Thus, it is possible to suppress deterioration of workability. Further, as a result of the mixing at 30° C. or lower, the galactose-partial degradation product can be easily dispersed in the aqueous solvent under the ordinary environment at room temperature without need for special conditions such as heating, and the aforementioned compound can be easily dissolved in the aqueous solvent, thereby enabling these steps to be performed by a simple operation. The aforementioned mixing may be performed while the heating is performed. Thus, it is possible to suppress deterioration of workability by mixing the galactose-partial degradation product and the aqueous solvent at 18 to 30° C.

The time for mixing together the aqueous solvent, the galactose-partial degradation product, and the aforementioned compound is not particularly limited and may be appropriately set when considering that the galactose-partial degradation product has a very good affinity to the aqueous solvent and the aforementioned compound is easily dissolved therein at the aforementioned temperature. The mixing time to be employed is, for example, 5 minutes to 1 hour, and preferably 10 minutes to 30 minutes. Setting the mixing time at 1 hour or less is advantageous in that the operation can be finished earlier and the workability can be improved.

According to step (1), it is also possible to obtain the gel composition as a molded article formed into a desired shape by transferring the mixture to a mold or the like having a desired shape before cooling or freezing in step (2).

In step (2), the mixture obtained in step (1) is cooled or frozen. More specifically, a hydrated swollen product in which the galactose-partial degradation product is hydrated and swollen in the aqueous solvent and the aforementioned compound is dissolved therein is obtained by cooling or freezing the dispersion liquid obtained in step (1). Examples of the hydrated swollen product include a hydrated swollen product in liquid form that has been cooled but not frozen and a hydrated swollen product in solid form that has been frozen. In step (2), the aqueous solvent may include a dissolved product resulting from partial dissolving of the galactose-partial degradation product.

According to step (2), the galactose-partial degradation product dispersed in the aqueous solvent in step (1) can be hydrated and swollen with water in the aqueous solvent by cooling or freezing the mixture of the aqueous solvent, the galactose-partial degradation product and the aforementioned compound. Since hydration and swelling can be thus produced, the development of viscosity can be relatively delayed, and thereby the galactose-partial degradation product can be dispersed in the aqueous solvent without need for forcible stirring with a relatively strong force as conventionally needed. Thus, the production method is simplified because the need for forcible stirring can be eliminated. In step (2), the aforementioned compound is dissolved in the aqueous solvent but may be partially undissolved. Also, in step (2), forcible stirring is not necessarily eliminated, but when forcible stirring is performed, the hydration and swelling of the galactose-partial degradation product can be more quickly produced than in the case of skipping the forcible stirring.

In the cooling or the freezing, the degree by which the temperature of the mixture is to be lowered is not particularly limited and may be appropriately set, provided that the galactose-partial degradation product in the mixture (dispersion liquid) obtained in step (1) can be hydrated and swollen. As the degree by which the temperature of the mixture is lowered is greater, the galactose-partial degradation product tends to be more easily hydrated and swollen, but on the other hand, the hydration and swelling excessively progresses to thereby cause the viscosity to be easily developed. In view of this aspect, it is preferable to cool or freeze the mixture obtained in step (1) to −25 to 10° C., for example. When the upper limit of the range of temperature, to which the temperature of the mixture is lowered, is set at 10° C. or lower, the galactose-partial degradation product is easily hydrated and swollen. The upper limit is more preferably 5° C., still more preferably 1° C. when considering that the hydration and swelling of the galactose-partial degradation product can be produced at such a temperature. On the other hand, when the lower limit of the range of temperature to which the temperature of the mixture is lowered is set at −25° C., excessive progress of hydration and swelling is suppressed, thereby making it hard for the viscosity to develop.

In step (3), the gel composition including the galactose-partial degradation product, the aforementioned compound and the aqueous solvent can be obtained by heating the mixture cooled or frozen in step (2), thereby gelling the same. More specifically, in step (3), the gel composition is obtained by heating the hydrated swollen product and the dissolved product obtained in step (2), thereby gelling the same.

In the heating, the degree by which the temperature of the cooled or frozen mixture (hydrated swollen product) obtained in step (2) is to be raised is not particularly limited and may be appropriately set, provided that the mixture is raised to a temperature at which the mixture can be fully gelled. As the degree by which the temperature of the mixture is raised is greater, the gel strength can be increased, but on the other hand, unnecessary heating operation is increased and hence the workability tends to be deteriorated. In view of this aspect, it is preferable to raise the temperature of the cooled or frozen mixture to 25 to 80° C., for example. The gel strength can be sufficiently increased by setting the lower limit of the range of temperature, to which the temperature of mixture is raised, at 25° C. The lower limit is more preferably 25° C., still more preferably 40° C. when considering that the gel strength can be more sufficiently increased. Meanwhile, when the upper limit of the range of temperature, to which the temperature of mixture is raised, is 80° C., unnecessary heating operation can be suppressed and hence the workability is suppressed from being deteriorated. The upper limit is still more preferably 50° C. from the aspect of suppressing unnecessary heating operations.

As mentioned above, the production method of this embodiment includes steps (1) to (3) mentioned below:

step (1) of mixing at room temperature a partial degradation product of the galactose moiety of galactoxyloglucan, a compound that is one kind or two or more kinds selected from the group consisting of magnesium salt, calcium salt, aluminum salt and sodium salt, and an aqueous solvent to obtain a mixture;

step (2) of cooling or freezing the mixture produced in step (1); and step (3) of gelling the mixture cooled or frozen in step (2) by heating to obtain a gel composition that includes the galactose-partial degradation product, the compound, and the aqueous solvent.

With such construction, in step (1), the partial degradation product of the galactose moiety of galactoxyloglucan is mixed with the aqueous solvent at room temperature so that the galactose-partial degradation product can be dispersed in the aqueous solvent without occurrence of undissolved lumps in the mixture, while the aforementioned compound is dissolved in the aqueous solvent. In step (2), the mixture obtained in step (1) is cooled or frozen, and thereby the galactose-partial degradation product can be hydrated and swollen in the aqueous solvent. At this time, the galactose-partial degradation product is easily brought into not the dissolved state but the hydrated swollen state. Thereby, it is possible to lower the viscosity of the mixture (dispersion liquid), and allow the mixture to be a hydrated swollen product having high viscosity by cooling or freezing the mixture. Further, since the development of viscosity can be relatively delayed, the galactose-partial degradation product can be fully dispersed in the aqueous solvent without need for forcible stirring with a relatively strong force as conventionally needed. Moreover, with steps (1) and (2), it is not necessary to cool the aqueous solvent in advance, and therefore time and labor for preparation can be eliminated. Then, in step (3), the mixture cooled or frozen in step (2) can be gelled by heating to produce a gelled mixture. The gel composition obtained this time is suppressed from having non-hydrated products such as undissolved lumps, which are caused by the galactose-partial degradation product, mixed therein. In step (3), when the cooled mixture is heated, it is preferable that the mixture be thawed by heating, then forcibly stirred, and then heated, and alternatively, it is preferable that the mixture be heated while being forcibly stirred after it is thawed by heating. Thus, a more homogeneous gel composition is obtainable by forcibly stirring while heating. Such forcible stirring is preferable particularly in step (3) for the galactose-partial degradation product having such a low concentration in which an aqueous layer is formed, and the gel composition can be more homogenized by being subjected to the forcible stirring. Accordingly, the method including steps (1) to (3) enables to easily produce the gel composition of this embodiment.

When an attempt is made to disperse a polysaccharide such as a locust bean gum in an aqueous solvent at room temperature, undissolved lumps may occur, which causes a lot of time or the necessity for heating to eliminate the undissolved lumps. Therefore, the polysaccharide needs to be dispersed by, for example, being forcibly stirred or heated after introduction into the aqueous solvent. After the dispersion, the mixture must be gelled by freezing and further thawing. However, if the heating is continued after the thawing, gel transfers to sol, and hence gel dissolves. On the other hand, the galactose-partial degradation product is not solated even if it is continuously heated after cooling, as mentioned above.

The galactose-partial degradation product used for the production method of this embodiment has reverse thermal gelation characteristics, as mentioned above, and specifically, has characteristics where it is gelled by heating around the body temperature. Thus, in the production method of this embodiment, the mixture (hydrated swollen product at a comparatively low temperature) obtained in step (2) may be applied to the skin to carry out the gelation in step (3) through the body temperature, for example. That is, the gel composition may be prepared when needed. The mixture (hydrated swollen product) after cooling or freezing in step (1) may be allowed to stand still for storage at a low temperature of 15° C. or lower until it is used in step (3) as needed. The thus stored mixture may be moved to a mold having a desired shape before heating in step (3), and then subjected to step (3) in this state to thereby obtain a gel composition as a molded article.

In the production method for the gel composition of this embodiment, the galactose-partial degradation product, the aforementioned compound, and the aqueous solvent are preferably mixed together at 18 to 30° C.

With such construction, the galactose-partial degradation product can be dispersed in the aqueous solvent in ordinary room-temperature environments, while further avoiding occurrence of undissolved lumps by mixing together the galactose-partial degradation product, the aforementioned compound, and the aqueous solvent at 18 to 30° C. Also, the aforementioned compound can be easily dissolved in the aqueous solvent. Accordingly, it is possible to suppress deterioration of workability.

In the production method for the gel composition of this embodiment, it is preferable that the galactose-partial degradation product be mixed with the aqueous solvent and thereafter further mixed with the aforementioned compound.

With such construction, the aforementioned compound can be mixed with a mixture in which the galactose-partial degradation product is fully dispersed in the aqueous solvent, and hence, more even mixing of the galactose-partial degradation product can be achieved, by mixing the galactose-partial degradation product with the aqueous solvent and thereafter further the aforementioned compound is mixed therewith. Thereby, the produced gel composition is allowed to easily exhibit elasticity and strength.

Next, a production method for the sheet of this embodiment will be described.

The production method for the sheet of this embodiment is a method for producing a sheet by drying the gel composition produced by the production method for the gel composition of the aforementioned embodiment using a specific inorganic compound among the aforementioned compounds.

Specifically, the production method for the sheet of this embodiment includes steps (1) to (3), using in step (1) an inorganic compound that is one kind or two or more kinds selected from the group consisting of magnesium salt, calcium salt and aluminum salt, and step (4) of drying the gel composition obtained through steps (1) to (3) to produce a sheet.

The drying temperature and the drying time may be appropriately set according to the content of the galactose-partial degradation product in the gel composition, the content of the inorganic compound, the thickness of the sheet, or the like.

The drying temperature is preferably 25° C. or higher, for example. The drying temperature is more preferably 30° C. or higher, still more preferably 40 to 80° C. when considering the possibility of shortening the drying time.

The drying time is preferably 3 to 10 hours when the drying temperature is 40 to 80° C., more preferably 10 to 30 hours when the drying temperature is 25 to 40° C.

The sheet may be produced by forming a gel composition, which has been obtained by heating the mixture obtained in step (2) to room temperature, into a sheet using an extrusion method such as a flat die method or calendar method, and then heating the gel composition to allow the same to be gelled and dried. The sheet may be also produced by allowing the mixture obtained in step (2) to flow onto a support body such as a film, drum or belt, and then heating it to produce a gel composition, and drying the gel composition. Moreover, in addition to the above, any device or means that is capable of producing the sheet having an even thickness can be appropriately employed.

In the production method for the sheet of this embodiment, the heating in step (3) and the drying in step (4) may be successively performed as an integrated operation.

As mentioned above, the production method for the sheet of this embodiment includes steps (1) to (4) mentioned below:

step (1) of mixing at room temperature a partial degradation product of the galactose moiety of galactoxyloglucan, an inorganic compound that is one kind or two or more kinds selected from the group consisting of magnesium salt, calcium salt and aluminum salt, and an aqueous solvent to obtain a mixture;

step (2) of cooling or freezing the mixture produced in step (1);

step (3) of gelling the mixture cooled or frozen in step (2) by heating to obtain a gel composition that includes the galactose-partial degradation product, the inorganic compound, and the aqueous solvent; and step (4) of drying the gel composition obtained in step (3) to produce a sheet.

With such construction, it is possible to easily produce a gel composition including a galactose-partial degradation product, an inorganic compound, and an aqueous solvent by performing steps (1) to (3), as mentioned above. It is also possible to produce a sheet only by drying in step (4) the gel composition obtained in step (3). Thus, the aforementioned production method for the sheet is simple.

In the production method for the sheet of this embodiment, the inorganic compound may further include sodium salt or potassium salt.

In step (1) in the production method for the sheet of this embodiment, the galactose-partial degradation product, the inorganic compound, and the aqueous solvent are mixed preferably at 18 to 30° C.

With such construction, it is possible to suppress deterioration of workability as mentioned above.

In step (1) in the production method for the sheet of this embodiment, it is preferable that the galactose-partial degradation product be mixed with the aqueous solvent and thereafter further mixed with the inorganic compound.

With such construction, as mentioned above, more uniform mixing of the galactose-partial degradation product can be achieved and thereby the obtained sheet can be allowed to easily exhibit sufficient flexibility and strength.

As mentioned above, according to these embodiments, a gel composition that is more excellent in elasticity and strength than ever, a sheet that is more excellent in flexibility and strength than ever, a production method that is capable of easily producing the gel composition, and a production method that is capable of easily producing the sheet are provided.

Since the gel composition and the sheet of these embodiments have characteristics where they can be produced by being gelled by heating, they are usable as a polymer material in various industries, such as those for domestic purposes, medical field, biomaterials, cosmetics (e.g. gel face pack) and hence usable in various fields. The galactose-partial degradation product used in these embodiments is not obtained by chemical modification of a natural substance derived galactoxyloglucan, and thus the obtained gel composition is also harmless to the living body.

The description for the gel composition, the sheet and the production methods therefor according to the embodiments was thus made, but the present invention is not limited to the aforementioned embodiments, and various modifications can be appropriately made within the intended scope of the present invention.

EXAMPLES

The present invention will be hereinafter described in detail with reference to examples but the present invention is not limited to those examples.

(Production Example 1) Production of a Partial Degradation Product of the Galactose Moiety of Galactoxyloglucan Purification of β-galactosidase:

A 2.5% aqueous solution of a commercially available β-galactosidase having complex enzyme activity "LACTASE Y-AO" [derived from Aspergillusoryzae, manufactured by Yakult Pharmaceutical Industry Co., Ltd.] was subjected to 0 to 0.6M NaCl gradient with 0.025 M phosphate buffer (pH 7.4) of an ion exchange chromatography

[DEAE Toyopeal, manufactured by Tosoh Corporation] to obtain eluate at a NaCl concentration of 0.2 to 0.4 M. Furthermore, the obtained eluate was subjected to 0 to 0.6M ammonium sulfate gradient with 0.025 M phosphate buffer (pH 7.4) of a hydrophobic chromatography [Butyl-Toyopeal, manufactured by Tosoh Corporation] to obtain eluate at an ammonium sulfate concentration of 10% or less. 60 mg of the purified enzyme was obtained from 2.5 g of a commercially available crude enzyme by these operations. Cellulase activity and IPase (isoprimeverose generation enzyme) activity were not found in this product.

Production of a Galactose-Partial Degradation Product:

Using the purified enzyme β-galactosidase obtained above, an aqueous solution of 1% substrate galactoxyloglucan [GLYLOID (registered trademark), manufactured by DSP GOKYO FOOD & CHEMICAL Co., Ltd.] was reacted at an enzyme concentration of $2.4 \times 10^{-5}$ mass %, a pH of 5.6, and a temperature of 50° C., and thereafter heated at 100° C. for 20 minutes to stop the reaction. The obtained reaction solution was gelled in about 15 hours after the reaction start, and, as a result, a gelled composition was obtained. The galactose removal ratio in the obtained gelled composition was calculated by the method below. 1 mL of a solution with 0.15 mass % of Cellulase Onozuka RS [manufactured by Yakult Pharmaceutical Industry Co., Ltd.] (50 mM acetic acid buffer solution, a pH of 4.0) was added to 7 g of an aqueous solution with 1 mass % of the gelled composition to react at 50° C. overnight. An aqueous solution with 1 mass % of galactoxyloglucan was also made to react in the same manner and an obtained product was employed as a control. After the reaction, the enzyme was deactivated by heating the reaction liquid for 30 minutes at 98° C. Then, a sample was subjected to a pretreatment cartridge [IC-SP, manufactured by Tosoh Corporation] and a membrane filter of 0.45 m cellulose acetate to obtain filtrate. 10 µL of the obtained filtrate was applied to an amino column of HPLC, in which acetonitrile:water=60:40 (v/v) was made to flow at 0.6 mL/min, so that elution areas of oligosaccharides (heptasaccharide (0 galactosemoiety), octasaccharide (1 galactose moiety), nonasaccharide (2 galactose moieties)) of galactoxyloglucan were detected using a refractive-index meter equipped therein. Then, the amount of galactose per unit (heptasaccharide) was calculated by an expression (area of octasaccharide+(area of nonasaccharide×2)/(area of heptasaccharide+area of octasaccharide+area of nonasaccharide). When the decreasing ratio of the amount of galactose determined on the gel composition from the amount of the galactose calculated from the control galactoxyloglucan was designated as the galactose removal ratio (%) and calculation was further made, the galactose removal ratio was found to be about 45%. Then, the thus obtained gelled composition was subjected to freeze dehydration, or was subjected to sedimentation and filtering subsequent to the addition of alcohol to the gelled composition, followed by drying, to obtain a galactose-partial degradation product in powder form.

In the following experimental examples, a gel composition produced to include the aforementioned compound and a galactose-partial degradation product was served as Example. Meanwhile, a gel composition produced to include a galactose-partial degradation product but not to include the aforementioned compound was served as Comparative Example.

Experimental Example 1

(1) Production of Gel Compositions of Examples 1 to 4

With a formulation shown in Table 1, 2.0 g (4 mass %) of the galactose-partial degradation product obtained in Production Example 1 was added into a plastic cup [EI-90, product name: PROMAX, content: 90 mL, manufactured by ASAHIKASEI PAX CORPORATION], and 2.0 g (4 mass %) of $MgCl_2$, $CaCl_2$, $AlCl_3$, or NaCl was further added thereto, followed by adding water at room temperature, to obtain a total amount of 50 g, which was stirred using a plastic stirrer (for about 10 seconds). Thereby, a dispersion liquid including a galactose-partial degradation product and an inorganic compound as the aforementioned compound was obtained. Then, 40 g of the obtained dispersion liquid was poured into a plastic dish having a diameter of 90 mm. The dispersion liquid in the plastic dish was allowed to stand still for 2 hours in a freezer [manufactured by HOSHIZAKI ELECTRIC CO., LTD., model: HRF-180XF] set at −20° C. to lower the temperature of the dispersion liquid to −20° C., then held for 2 hours in this state, and then thawed at room temperature. After thawing, the dispersion liquid was heated overnight at 40° C. or for 1 to 2 hours at 80° C. to produce a gel composition. After heating, this sample was allowed to stand still at room temperature to have its temperature lowered to the room temperature. Visual observation revealed that the obtained composition was surely gelled.

(2) Production of Gel Composition of Comparative Example 1

Gel compositions were produced in the same manner as Examples 1 to 4 with the formulation shown in Table 1 except that an inorganic compound as the aforementioned compound was not included. Visual observation revealed that the obtained composition was surely gelled.

(3) Production of Gel Compositions of Comparative Examples 2 and 3

Gel compositions were produced in the same manner as Examples 1 to 4 with the formulation shown in Table 1 except that galactoxyloglucan [manufactured by DSP GOKYO FOOD & CHEMICAL Co., Ltd., GLYLOID (registered trademark)] was used instead of the galactose-partial degradation product, or the galactose-partial degradation product was used while the inorganic compound was not used, or the galactoxyloglucan was used instead of the galactose-partial degradation product while the inorganic compound was not used. Visual observation revealed that the obtained compositions were not gelled but solated with a thickness.

(4) Evaluation

After the heating as mentioned above, the gel compositions were allowed to stand still at room temperature (20 to 25° C.) for several days. Thereafter, evaluations mentioned below were made in terms of the physical properties of the gel compositions. The results are shown in Table 1. The heat resistance was almost the same as the conventional one, and deterioration in heat resistance was not found. Further, evaluation was made in terms of the water content as shown below, and it was found that the water content of $MgCl_2$ containing gel (Example 1) was 83.7 mass %, the water content of $CaCl_2$ containing gel (Example 2) was 80.4 mass %, the water content of $AlCl_3$ containing gel (Example 3) was 82.3 mass %, and the water content of NaCl containing gel (Example 4) was 84.2 mass %. The water content of the composition of Comparative Example 1 was 92.5 mass %.

Water Content

The water contents of the gel compositions were measured as follows: each gel composition was dried under a reduced pressure of −0.1 MPa (atmospheric pressure basis) at 70° C. for 8 to 12 hours, and then the ratio of the decrement in weight after drying relative to the weight before drying, which was measured in advance, was calculated.

Gel Formation

Each formed gel at room temperature was checked by touching with hand, and evaluation was made on the formed gel according to the following evaluation criteria.

Not broken: ○
Slightly easily broken: Δ
Easily broken: x

Elasticity

Each gel at room temperature was deformed to a certain degree by pushing it with finger to check the elasticity based on such physical contact, and evaluation was made on the elasticity according to the following evaluation criteria.

Having very high elasticity: ◎
Having certain elasticity: ○
Having insufficient elasticity: Δ
Having no elasticity: x Tensile Tear Resistance (Strength)

Each gel at room temperature was held by both hands and were given a laterally outer force to check the tensile tear resistance, and evaluation was made on the tensile tear resistance according to the following evaluation criteria.

Hardly torn: ○
Easily torn: x

Water Resistance

Each gel was immersed in water overnight to check the water resistance, and evaluation was made on the water resistance according to the following evaluation criteria.

Shape is not broken at all: having water resistance: ○
Shape is broken: having no water resistance: x Comprehensive Evaluation Comprehensive evaluation was made by classifying the evaluations of the respective evaluation items and the number(s) of the evaluations as shown below, and judgment was made according to the following criteria.

One or more objects evaluated as ◎: very excellent: ◎
No objects evaluated as x: good: ○
One object evaluated as x: almost good: Δ
Two or more objects evaluated as x: poor: x

TABLE 1

| | Inorganic salt | mass % | Polysaccharide | Mass % | Input amount (g) | Temperature (° C.) | Composition type | Evaluation | | | | |
|---|---|---|---|---|---|---|---|---|---|---|---|---|
| | | | | | | | | Gel formation | Elasticity | Tensile tear-resistance | Water resistance | Comprehensive evaluation |
| Com. Ex. 1 | nil | 0 | partial degradation product | 4 | 40 | 80 | gel | ○ | Δ | X | ○ | Δ |
| Ex. 1 | MgCl₂ | 4 | partial degradation product | 4 | 40 | 80 | gel | ○ | ◎ | ○ | ○ | ◎ |
| Ex. 2 | CaCl₂ | 4 | partial degradation product | 4 | 40 | 80 | gel | ○ | ◎ | ○ | ○ | ◎ |
| Ex. 3 | AlCl₃ | 4 | partial degradation product | 4 | 40 | 80 | gel | ○ | ◎ | ○ | ○ | ◎ |
| Ex. 4 | NaCl | 4 | partial degradation product | 4 | 40 | 80 | gel | ○ | Δ | X | ○ | Δ |
| Com. Ex. 2 | nil | 0 | GLYLOID | 4 | 40 | 80 | thick sol | X | X | X | X | X |
| Com. Ex. 3 | MgCl₂ | 4 | GLYLOID | 4 | 40 | 80 | thick sol | X | X | X | X | X |

As shown in Table 1, it was found that the gel compositions of Examples 1 to 3 each obtained from a dispersion liquid that has a composition of 4 mass % of a galactose-partial degradation product and 4 mass % of an inorganic compound ($MgCl_2$, $CaCl_2$, or $AlCl_3$) have high elasticity and strength, and are very excellent gel compositions. Gel compositions having sufficient elasticity and strength could not be obtained from Example 4 in which a gel composition includes NaCl and Comparative Example 1 in which an inorganic composition is not added to a gem composition. The gel composition of Comparative Example 3 was not gelled. All of the gel compositions of Examples 1 to 4 including the galactose-partial degradation product and the inorganic compound exhibited water resistance. Shapes of the gel compositions of Example 4, and Comparative Examples 1 and 2 were broken with touch of finger of hand. Examples 1 and 3 were superior to Example 2, and Example 1 was almost the same as Example 3 in terms of the elasticity evaluated based on the physical contact of finger of hand, and the tensile tear-resistance.

Gel compositions of Comparative Examples 2 and 3 produced in the same manner as the aforementioned Examples using galactoxyloglucan [manufactured by DSP GOKYO FOOD & CHEMICAL Co., Ltd., GLYLOID (registered trademark)] in which a galactose moiety is not removed were not gelled regardless whether the gel composition includes $MgCl_2$ or not. Thus, it was found that the combination of the galactose-partial degradation product and the inorganic compound ($MgCl_2$, $CaCl_2$, or $AlCl_3$) is necessary to impart elasticity and strength to the gel composition.

Experimental Example 2

(1) Production of Sheets of Examples 5 to 63

As shown in Tables 2 to 6, sheets were produced by drying gel compositions in the same manner as Examples 1 to 4, except that 0.5 g (1 mass %) to 2.5 g (5 mass %) of a galactose-partial degradation product was mixed, and 0.25 g (0.5 mass %) to 6.0 g (12 mass %) of $MgCl_2$, $CaCl_2$, $AlCl_3$, or NaCl was mixed, and a total of 5 g, 7 g, 10 g, or 20 g thereof was poured into the plastic dish to be dried by heating overnight at 40° C. or for 3 to 4 hours at 80° C. In Tables 2 to 6, the partial degradation product is denoted by "part".

(2) Production of Sheets of Comparative Examples 4 to 41

Sheets were produced in the same manner as Examples 1 to 4 with a formulation shown in Table 7, except that galactoxyloglucan [manufactured by DSP GOKYO FOOD & CHEMICAL Co., Ltd., GLYLOID (registered trademark)] was used instead of a galactose-partial degradation product, or a galactose-partial degradation product was used while an inorganic compound was not used, or the aforementioned galactoxyloglucan was used instead of a galactose-partial degradation product while an inorganic compound was not used. In Table 7, GLYLOID is denoted by "G".

(3) Evaluation

Sheets were heated as mentioned above and allowed to stand still at room temperature (20 to 25° C.) for one day or more, and thereafter evaluation was made on physical properties in terms of items below. The results are shown in Tables 2 to 7. Evaluation made on water content in the manner as shown below revealed that the water content of Example 39 was 16.2 mass %, and the water content of Example 41 was 16.5 mass %, while the water content of comparative example 26 which does not include an inorganic compound was 7.4 mass %. That is, it was found that a sheet that does not include an inorganic compound cannot contain plenty of water therein.

Water Content

The water contents of the sheets were measured as follows: each produced sheet was dried under a reduced pressure of −0.1 MPa (atmospheric pressure basis) at 70° C. for 8 to 12 hours, and then the ratio of the decrement in weight of sheet after drying relative to the weight before drying, which was measured in advance, was calculated.

Checking Whether any of S (Including GS) and F (GSF Formation) has been Formed

Whether a sheet was formed or not was checked by visual observation or physical contact, and evaluation was made according to the following evaluation criteria.

Sheet is formed: ○
Sheet is insufficiently formed: Δ
Sheet is not formed: x

Classification of Sheet

Formed sheets and insufficiently formed sheets were classified based on the checking by visual observation and physical contact mentioned above, and the thickness of each sheet was measured according to JIS K7130. A sheet having a thickness of less than 0.25 mm (250 micrometers) was indicated by "F", and a sheet having a thickness of 0.25 mm or more was indicated by "S." A sheet containing sufficient water which was confirmed based on the checking by visual observation and physical contact was designated as a gelled sheet and indicated by "GS".

Flexibility

The flexibility of each produced sheet was examined by physical contact, and evaluation was made on the flexibility according to the following evaluation criteria.

Freely bendable: very high: ⊚
Easily bendable: high: ○
Bendable by application of slight force: almost flexible: Δ
Not bendable even by application of a force to bend: insufficient: x Extensibility The extensibility of each produced sheet was examined by pulling the sheet by hand, and evaluation was made on the extensibility according to the following evaluation criteria.

Very easily stretchable: very high: ⊚
Easily stretchable: high: ○
Stretchable by applying a slight force to pull: almost stretchable: Δ
Not stretchable even by applying a force to pull: not stretchable: x Cracking Resistance The cracking resistance of each produced sheet was examined by bending the sheet by hand, and evaluation was made on the cracking resistance according to the following evaluation criteria.

Not cracked: ○
Hardly cracked: Δ
Easily cracked: x

Tensile Tear Resistance (strength)

The tensile tear resistance of each produced sheet was examined by applying a lateral outward force to the sheet while holding the same at room temperature by both hands, and evaluation was made on the tensile tear resistance according to the following evaluation criteria.

Very hardly tearable: ○
Almost hardly tearable: Δ
Easily tearable: x

Water Resistance

The water resistance was examined by immersing each produced sheet overnight, and evaluation was made on the water resistance according to the following evaluation criteria.

Shape is not broken at all: having water resistance: ○
Shape is broken: having no water resistance: x Adhesiveness to Container After Heating The adhesiveness of each produced sheet to a bottom of a container that is served as a mold was examined by visually checking whether the sheet adheres to the bottom of the container after heating, and evaluation was made on the adhesiveness to the container after heating according to the following evaluation criteria.

Adhering to the container: ○
Not adhering to the container: x

Re-adhesiveness to Container (Adhesiveness (tackiness))

The re-adhesiveness of each produced sheet to a bottom of a container was examined according to the following evaluation criteria by removing the sheet from a container, then slightly pressing the sheet to the bottom of the same container, and then visually checking whether the sheet adheres to the bottom of the container.

Re-adhered: ○
Not re-adhered: x

Transparency

The transparency was examined by visually observing each produced sheet, and evaluation was made on the transparency according to the following evaluation criteria.

When the sheet is placed on the back of a hand, the skin can be clearly seen through the sheet: having transparency: ○
When the sheet is placed on the back of a hand, the skin cannot be clearly seen through the sheet: having no transparency: x Comprehensive Evaluation Comprehensive evaluation was made by classifying the evaluations of the respective evaluation items other than the transparency, the adhesiveness to the container after heating, the re-adhesiveness to the container, and the GSF formation, and the number(s) of the evaluations, and judgment was made according to the following criteria.

No object evaluated as x, one or more objects evaluated as ◎, and one or less object evaluated as △: very excellent: ◎

No object evaluated as x, no object evaluated as ◎, and two or more objects evaluated as ○: good: ○

One or more objects evaluated as x: poor: x

TABLE 2

| | Inorganic salt/ mass % | Polysaccharide/ mass % | Input amount (g) | Temperature (° C.) | Evaluation | | | |
|---|---|---|---|---|---|---|---|---|
| | | | | | GSF formation | Sheet classification | Flexibility | Extensibility |
| Com. Ex. 4 | nil | 0 part | 1 | 5 | 80 | ○ | F | △ | X |
| Com. Ex. 5 | nil | 0 part | 1 | 10 | 80 | ○ | F | △ | X |
| Com. Ex. 6 | nil | 0 part | 1 | 10 | 40 | ○ | F | △ | X |
| Com. Ex. 7 | nil | 0 part | 1 | 20 | 80 | ○ | F | △ | X |
| Com. Ex. 8 | nil | 0 part | 1 | 20 | 40 | ○ | F | X | X |
| Ex. 5 | $MgCl_2$ | 0.5 part | 1 | 5 | 80 | ○ | F | ◎ | ◎ |
| Ex. 6 | $MgCl_2$ | 0.5 part | 1 | 10 | 80 | ○ | F | ◎ | ◎ |
| Ex. 7 | $MgCl_2$ | 0.5 part | 1 | 10 | 40 | ○ | F | ◎ | ○ |
| Ex. 8 | $MgCl_2$ | 0.5 part | 1 | 20 | 80 | ○ | F | ◎ | ◎ |
| Ex. 9 | $MgCl_2$ | 0.5 part | 1 | 20 | 40 | ○ | F | ◎ | ○ |
| Com. Ex. 9 | nil | 0 part | 2 | 5 | 80 | ○ | F | △ | X |
| Com. Ex. 10 | nil | 0 part | 2 | 10 | 80 | ○ | F | △ | X |
| Com. Ex. 11 | nil | 0 part | 2 | 10 | 40 | ○ | F | X | X |
| Com. Ex. 12 | nil | 0 part | 2 | 20 | 80 | ○ | F | X | X |
| Com. Ex. 13 | nil | 0 part | 2 | 20 | 40 | ○ | F | X | X |
| Ex. 10 | $MgCl_2$ | 1 part | 2 | 5 | 80 | ○ | F | ◎ | ◎ |
| Ex. 11 | $MgCl_2$ | 1 part | 2 | 10 | 80 | ○ | F | ◎ | ◎ |
| Ex. 12 | $MgCl_2$ | 1 part | 2 | 10 | 40 | ○ | F | ◎ | ○ |
| Ex. 13 | $MgCl_2$ | 1 part | 2 | 20 | 80 | ○ | F | ◎ | ○ |
| Ex. 14 | $MgCl_2$ | 1 part | 2 | 20 | 40 | ○ | F | ◎ | ○ |

| | Evaluation | | | | | | |
|---|---|---|---|---|---|---|---|
| | Cracking resistance | Tensile tear-resistance | Water resistance | Adhesiveness to container after heating | Re-adhesiveness to container | Transparency | Comprehensive evaluation |
| Com. Ex. 4 | X | X | ○ | X | X | ○ | X |
| Com. Ex. 5 | X | △ | ○ | X | X | ○ | X |
| Com. Ex. 6 | X | ○ | ○ | X | X | ○ | X |
| Com. Ex. 7 | X | X | ○ | X | X | ○ | X |
| Com. Ex. 8 | X | ○ | ○ | X | X | ○ | X |
| Ex. 5 | ○ | ○ | ○ | ○ | ○ | ○ | ◎ |
| Ex. 6 | ○ | ○ | ○ | ○ | ○ | ○ | ◎ |
| Ex. 7 | ○ | ○ | ○ | ○ | X | ○ | ◎ |
| Ex. 8 | ○ | ○ | ○ | ○ | ○ | ○ | ◎ |
| Ex. 9 | ○ | ○ | ○ | ○ | X | ○ | ◎ |
| Com. Ex. 9 | X | △ | ○ | X | X | ○ | X |
| Com. Ex. 10 | X | ○ | ○ | X | X | ○ | X |
| Com. Ex. 11 | X | ○ | ○ | X | X | ○ | X |
| Com. Ex. 12 | X | X | ○ | X | X | ○ | X |
| Com. Ex. 13 | X | ○ | ○ | X | X | ○ | X |
| Ex. 10 | ○ | ○ | ○ | ○ | X | ○ | ◎ |
| Ex. 11 | ○ | ○ | ○ | ○ | X | ○ | ◎ |
| Ex. 12 | ○ | ○ | ○ | ○ | X | ○ | ◎ |
| Ex. 13 | ○ | ○ | ○ | ○ | X | ○ | ◎ |
| Ex. 14 | ○ | ○ | ○ | ○ | X | ○ | ◎ |

TABLE 3

| | Inorganic salt, mass % | Polysaccharide, mass % | Input amount (g) | Temperature (° C.) | Evaluation | | | |
|---|---|---|---|---|---|---|---|---|
| | | | | | GSF formation | Sheet classification | Flexibility | Extensibility |
| Com. Ex. 14 | nil | 0 part | 3 | 5 | 80 | ○ | F | △ | X |
| Com. Ex. 15 | nil | 0 part | 3 | 5 | 40 | ○ | F | △ | X |
| Com. Ex. 16 | nil | 0 part | 3 | 7 | 80 | ○ | F | △ | X |
| Com. Ex. 17 | nil | 0 part | 3 | 10 | 80 | ○ | F | X | X |
| Com. Ex. 18 | nil | 0 part | 3 | 10 | 40 | ○ | F | △ | X |
| Com. Ex. 19 | nil | 0 part | 3 | 20 | 80 | ○ | F | X | X |
| Com. Ex. 20 | nil | 0 part | 3 | 20 | 40 | ○ | F | X | X |
| Ex. 15 | $MgCl_2$ | 1 part | 3 | 7 | 80 | ○ | F | ◎ | △ |

TABLE 3-continued

| | | | | | | | | | | |
|---|---|---|---|---|---|---|---|---|---|---|
| Ex. 16 | MgCl$_2$ | 1 | part | 3 | 20 | 80 | ○ | F | ◎ | △ |
| Ex. 17 | MgCl$_2$ | 2 | part | 3 | 7 | 80 | ○ | F | ◎ | ○ |
| Ex. 18 | MgCl$_2$ | 2 | part | 3 | 20 | 80 | ○ | F | ◎ | ○ |
| Ex. 19 | MgCl$_2$ | 4 | part | 3 | 5 | 80 | ○ | F | ◎ | ◎ |
| Ex. 20 | MgCl$_2$ | 4 | part | 3 | 5 | 40 | ○ | F | ◎ | ◎ |
| Ex. 21 | MgCl$_2$ | 4 | part | 3 | 7 | 80 | ○ | F | ◎ | ○ |
| Ex. 22 | MgCl$_2$ | 4 | part | 3 | 10 | 80 | ○ | F | ◎ | ◎ |
| Ex. 23 | MgCl$_2$ | 4 | part | 3 | 10 | 40 | ○ | F | ◎ | ◎ |
| Ex. 24 | MgCl$_2$ | 4 | part | 3 | 20 | 80 | ○ | S | ◎ | ◎ |
| Ex. 25 | MgCl$_2$ | 4 | part | 3 | 20 | 40 | ○ | F | ◎ | ◎ |
| Ex. 26 | MgCl$_2$ | 6 | part | 3 | 20 | 80 | ○ | S | ◎ | ◎ |

| | Evaluation | | | | | | |
|---|---|---|---|---|---|---|---|
| | Cracking resistance | Tensile tear-resistance | Water resistance | Adhesiveness to container after heating | Re-adhesiveness to container | Transparency | Comprehensive evaluation |
| Com. Ex. 14 | X | ○ | ○ | ○ | X | ○ | X |
| Com. Ex. 15 | X | ○ | ○ | X | X | ○ | X |
| Com. Ex. 16 | X | ○ | ○ | X | X | ○ | X |
| Com. Ex. 17 | X | ○ | ○ | X | X | ○ | X |
| Com. Ex. 18 | X | ○ | ○ | X | X | ○ | X |
| Com. Ex. 19 | X | ○ | ○ | X | X | ○ | X |
| Com. Ex. 20 | X | ○ | ○ | X | X | ○ | X |
| Ex. 15 | ○ | ○ | ○ | ○ | X | ○ | ◎ |
| Ex. 16 | ○ | ○ | ○ | ○ | X | ○ | ◎ |
| Ex. 17 | ○ | ○ | ○ | ○ | X | ○ | ◎ |
| Ex. 18 | ○ | ○ | ○ | ○ | X | ○ | ◎ |
| Ex. 19 | ○ | △ | ○ | ○ | ○ | ○ | ◎ |
| Ex. 20 | ○ | ○ | ○ | ○ | ○ | ○ | ◎ |
| Ex. 21 | ○ | ○ | ○ | ○ | ○ | ○ | ◎ |
| Ex. 22 | ○ | ○ | ○ | ○ | ○ | ○ | ◎ |
| Ex. 23 | ○ | ○ | ○ | ○ | ○ | ○ | ◎ |
| Ex. 24 | ○ | ○ | ○ | ○ | ○ | ○ | ◎ |
| Ex. 25 | ○ | ○ | ○ | ○ | ○ | ○ | ◎ |
| Ex. 26 | ○ | △ | ○ | ○ | ○ | ○ | ◎ |

TABLE 4

| | Inorganic salt, mass % | polysaccharide, mass % | | amount (g) | Temperature (° C.) | GSF formation | Sheet classification | Flexibility | Extensibility | Cracking resistance |
|---|---|---|---|---|---|---|---|---|---|---|
| Com. Ex. 21 | nil | 0 | part | 4 | 5 | 40 | ○ | F | △ | X | X |
| Com. Ex. 22 | nil | 0 | part | 4 | 7 | 80 | ○ | F | △ | X | X |
| Com. Ex. 23 | nil | 0 | part | 4 | 10 | 80 | ○ | F | X | X | X |
| Com. Ex. 24 | nil | 0 | part | 4 | 10 | 40 | ○ | F | X | X | X |
| Com. Ex. 25 | nil | 0 | part | 4 | 20 | 80 | ○ | S | X | X | X |
| Com. Ex. 26 | nil | 0 | part | 4 | 20 | 40 | ○ | F | X | X | X |
| Ex. 27 | MgCl$_2$ | 1 | part | 4 | 7 | 80 | ○ | F | ◎ | ○ | △ |
| Ex. 28 | MgCl$_2$ | 1 | part | 4 | 20 | 80 | ○ | F | ○ | △ | △ |
| Ex. 29 | MgCl$_2$ | 2 | part | 4 | 7 | 80 | ○ | F | ◎ | ○ | ○ |
| Ex. 30 | MgCl$_2$ | 2 | part | 4 | 20 | 80 | ○ | GS | ◎ | ○ | ○ |
| Ex. 31 | MgCl$_2$ | 4 | part | 4 | 5 | 80 | ○ | F | ◎ | ◎ | ○ |
| Ex. 32 | MgCl$_2$ | 4 | part | 4 | 5 | 40 | ○ | F | ◎ | ◎ | ○ |
| Ex. 33 | MgCl$_2$ | 4 | part | 4 | 7 | 80 | ○ | F | ◎ | ◎ | ○ |
| Ex. 34 | MgCl$_2$ | 4 | part | 4 | 10 | 80 | ○ | F | ◎ | ◎ | ○ |
| Ex. 35 | MgCl$_2$ | 4 | part | 4 | 10 | 40 | ○ | F | ◎ | ◎ | ○ |
| Ex. 36 | CaCl$_2$ | 4 | part | 4 | 10 | 40 | ○ | F | ◎ | ◎ | ○ |
| Ex. 37 | AlCl$_3$ | 4 | part | 4 | 10 | 40 | ○ | F | ◎ | ◎ | ○ |
| Com. Ex. 27 | NaCl | 4 | part | 4 | 10 | 40 | ○ | F | X | X | X |

| | Evaluation | | | | | |
|---|---|---|---|---|---|---|
| | Tensile tear-resistance | Water resistance | Adhesiveness to container after heating | Re-adhesiveness to container | Transparency | Comprehensive evaluation |
| Com. Ex. 21 | ○ | ○ | X | X | ○ | X |
| Com. Ex. 22 | ○ | ○ | X | X | ○ | X |
| Com. Ex. 23 | ○ | ○ | X | X | ○ | X |
| Com. Ex. 24 | ○ | ○ | X | X | ○ | X |
| Com. Ex. 25 | ○ | ○ | X | X | ○ | X |
| Com. Ex. 26 | ○ | ○ | X | X | ○ | X |

TABLE 4-continued

| | | | | | | |
|---|---|---|---|---|---|---|
| Ex. 27 | ○ | ○ | ○ | X | ○ | ◎ |
| Ex. 28 | ○ | ○ | ○ | X | ○ | ○ |
| Ex. 29 | ○ | ○ | ○ | X | ○ | ◎ |
| Ex. 30 | ○ | ○ | ○ | X | ○ | ◎ |
| Ex. 31 | Δ | ○ | ○ | ○ | ○ | ◎ |
| Ex. 32 | ○ | ○ | ○ | ○ | ○ | ◎ |
| Ex. 33 | ○ | ○ | ○ | ○ | ○ | ◎ |
| Ex. 34 | ○ | ○ | ○ | ○ | ○ | ◎ |
| Ex. 35 | ○ | ○ | ○ | ○ | ○ | ◎ |
| Ex. 36 | Δ | ○ | ○ | ○ | ○ | ◎ |
| Ex. 37 | Δ | ○ | ○ | ○ | ○ | ◎ |
| Com. Ex. 27 | ○ | ○ | X | X | X | X |

TABLE 5

| | Inorganic salt, mass % | | polysaccharide, mass % | | Input amount (g) | Temperature (° C.) | Evaluation | | | |
|---|---|---|---|---|---|---|---|---|---|---|
| | | | | | | | GSF formation | Sheet classification | Flexibility | Extensibility |
| Ex. 38 | $MgCl_2$ | 4 | part | 4 | 20 | 80 | ○ | S | ◎ | ◎ |
| Ex. 39 | $MgCl_2$ | 4 | part | 4 | 20 | 40 | ○ | S | ◎ | ◎ |
| Ex. 40 | $CaCl_2$ | 4 | part | 4 | 20 | 40 | ○ | S | ◎ | ◎ |
| Ex. 41 | $AlCl_3$ | 4 | part | 4 | 20 | 40 | ○ | S | ◎ | ◎ |
| Com. Ex. 28 | NaCl | 4 | part | 4 | 20 | 40 | ○ | F | X | X |
| Ex. 42 | $MgCl_2$ | 6 | part | 4 | 20 | 80 | ○ | GS | ◎ | ◎ |
| Ex. 43 | $MgCl_2$ | 8 | part | 4 | 20 | 80 | ○ | GS | ◎ | ◎ |
| Ex. 44 | $MgCl_2$ | 10 | part | 4 | 20 | 80 | ○ | GS | ◎ | ◎ |
| Ex. 45 | $MgCl_2$ | 12 | part | 4 | 20 | 80 | ○ | GS | ◎ | ◎ |
| Com. Ex. 29 | nil | 0 | part | 5 | 4 | 80 | ○ | F | Δ | X |
| Com. Ex. 30 | nil | 0 | part | 5 | 4 | 40 | ○ | F | Δ | X |
| Com. Ex. 31 | nil | 0 | part | 5 | 5 | 80 | ○ | F | X | X |
| Com. Ex. 32 | nil | 0 | part | 5 | 5 | 40 | ○ | F | Δ | X |
| Com. Ex. 33 | nil | 0 | part | 5 | 7 | 80 | ○ | F | Δ | X |
| Com. Ex. 34 | nil | 0 | part | 5 | 10 | 80 | ○ | F | X | X |
| Com. Ex. 35 | nil | 0 | part | 5 | 10 | 40 | ○ | F | X | X |

| | Evaluation | | | | | | |
|---|---|---|---|---|---|---|---|
| | Cracking resistance | Tensile tear-resistance | Water resistance | Adhesiveness to container after heating | Re-adhesiveness to container | Transparency | Comprehensive evaluation |
| Ex. 38 | ○ | ○ | ○ | ○ | ○ | ○ | ◎ |
| Ex. 39 | ○ | ○ | ○ | ○ | ○ | ○ | ◎ |
| Ex. 40 | ○ | ○ | ○ | ○ | ○ | ○ | ◎ |
| Ex. 41 | ○ | Δ | ○ | ○ | ○ | ○ | ◎ |
| Com. Ex. 28 | X | ○ | ○ | X | X | X | X |
| Ex. 42 | ○ | ○ | ○ | ○ | ○ | ○ | ◎ |
| Ex. 43 | ○ | Δ | ○ | ○ | ○ | ○ | ◎ |
| Ex. 44 | ○ | Δ | ○ | ○ | ○ | ○ | ◎ |
| Ex. 45 | ○ | Δ | ○ | ○ | ○ | ○ | ◎ |
| Com. Ex. 29 | X | X | ○ | X | X | ○ | X |
| Com. Ex. 30 | X | X | ○ | X | X | ○ | X |
| Com. Ex. 31 | X | ○ | ○ | X | X | ○ | X |
| Com. Ex. 32 | X | ○ | ○ | X | X | ○ | X |
| Com. Ex. 33 | X | ○ | ○ | X | X | ○ | X |
| Com. Ex. 34 | X | ○ | ○ | X | X | ○ | X |
| Com. Ex. 35 | X | ○ | ○ | X | X | ○ | X |

TABLE 6

| | Inorganic salt, mass % | | Polysaccharide, mass % | | Input amount (g) | Temperature (° C.) | Evaluation | | | |
|---|---|---|---|---|---|---|---|---|---|---|
| | | | | | | | GSF formation | Sheet classification | Flexibility | Extensibility |
| Com. Ex. 36 | nil | 0 | part | 5 | 20 | 80 | ○ | F | X | X |
| Com. Ex. 37 | nil | 0 | part | 5 | 20 | 40 | ○ | F | X | X |
| Ex. 46 | $MgCl_2$ | 1 | part | 5 | 7 | 80 | ○ | F | ○ | Δ |
| Ex. 47 | $MgCl_2$ | 1 | part | 5 | 20 | 80 | ○ | F | Δ | Δ |
| Ex. 48 | $MgCl_2$ | 2 | part | 5 | 7 | 80 | ○ | F | ◎ | ○ |
| Ex. 49 | $MgCl_2$ | 2 | part | 5 | 20 | 80 | ○ | S | ◎ | ○ |
| Ex. 50 | $MgCl_2$ | 4 | part | 5 | 4 | 80 | ○ | F | ◎ | ◎ |
| Ex. 51 | $MgCl_2$ | 4 | part | 5 | 4 | 40 | ○ | F | ◎ | ◎ |

TABLE 6-continued

| | Inorganic salt | amount | | Polysaccharide mass % | Input amount | Temperature | GSF formation | Sheet classification | Flexibility | Extensibility |
|---|---|---|---|---|---|---|---|---|---|---|
| Ex. 52 | $MgCl_2$ | 4 | part | 5 | 5 | 80 | ○ | F | ◎ | ◎ |
| Ex. 53 | $MgCl_2$ | 4 | part | 5 | 5 | 40 | ○ | F | ◎ | ◎ |
| Ex. 54 | $MgCl_2$ | 4 | part | 5 | 10 | 80 | ○ | S | ◎ | ◎ |
| Ex. 55 | $MgCl_2$ | 4 | part | 5 | 10 | 40 | ○ | S | ◎ | ◎ |
| Ex. 56 | $MgCl_2$ | 4 | part | 5 | 20 | 80 | ○ | S | ◎ | ◎ |
| Ex. 57 | $MgCl_2$ | 4 | part | 5 | 20 | 40 | ○ | S | ◎ | ◎ |
| Ex. 58 | $MgCl_2$ | 6 | part | 5 | 7 | 80 | ○ | GS | ◎ | ◎ |
| Ex. 59 | $MgCl_2$ | 6 | part | 5 | 20 | 80 | ○ | GS | ◎ | ◎ |
| Ex. 60 | $MgCl_2$ | 8 | part | 5 | 7 | 80 | ○ | GS | ◎ | ◎ |
| Ex. 61 | $MgCl_2$ | 8 | part | 5 | 20 | 80 | ○ | GS | ◎ | ◎ |
| Ex. 62 | $MgCl_2$ | 10 | part | 5 | 20 | 80 | ○ | GS | ◎ | ◎ |
| Ex. 63 | $MgCl_2$ | 12 | part | 5 | 20 | 80 | ○ | GS | ◎ | ◎ |

| | Evaluation | | | | | | |
|---|---|---|---|---|---|---|---|
| | Cracking resistance | Tensile tear-resistance | Water resistance | Adhesiveness to container after heating | Re-adhesiveness to container | Transparency | Comprehensive evaluation |
| Com. Ex. 36 | X | ○ | ○ | X | X | ○ | X |
| Com. Ex. 37 | X | ○ | ○ | X | X | ○ | X |
| Ex. 46 | Δ | ○ | ○ | X | X | ○ | ○ |
| Ex. 47 | Δ | ○ | ○ | X | X | ○ | ○ |
| Ex. 48 | ○ | ○ | ○ | ○ | X | ○ | ◎ |
| Ex. 49 | ○ | ○ | ○ | ○ | X | ○ | ◎ |
| Ex. 50 | ○ | ○ | ○ | ○ | ○ | ○ | ◎ |
| Ex. 51 | ○ | ○ | ○ | ○ | ○ | ○ | ◎ |
| Ex. 52 | ○ | ○ | ○ | ○ | ○ | ○ | ◎ |
| Ex. 53 | ○ | ○ | ○ | ○ | ○ | ○ | ◎ |
| Ex. 54 | ○ | ○ | ○ | ○ | ○ | ○ | ◎ |
| Ex. 55 | ○ | ○ | ○ | ○ | ○ | ○ | ◎ |
| Ex. 56 | ○ | ○ | ○ | ○ | ○ | ○ | ◎ |
| Ex. 57 | ○ | ○ | ○ | ○ | ○ | ○ | ◎ |
| Ex. 58 | ○ | Δ | ○ | ○ | ○ | ○ | ◎ |
| Ex. 59 | ○ | Δ | ○ | ○ | ○ | ○ | ◎ |
| Ex. 60 | ○ | Δ | ○ | ○ | ○ | ○ | ◎ |
| Ex. 61 | ○ | ○ | ○ | ○ | ○ | ○ | ◎ |
| Ex. 62 | ○ | Δ | ○ | ○ | ○ | ○ | ◎ |
| Ex. 63 | ○ | Δ | ○ | ○ | ○ | ○ | ◎ |

TABLE 7

| | Inorganic salt, mass % | Polysaccharide, mass % | Input amount (g) | Temperature (° C.) | GSF formation | Sheet classification | Flexibility | Extensibility |
|---|---|---|---|---|---|---|---|---|
| Com. Ex. 38 | nil | 0 | G | 4 | 10 | 40 | ○ | F | Δ | X |
| Com. Ex. 39 | $MgCl_2$ | 4 | G | 4 | 10 | 40 | X | — | ◎ | ◎ |
| Com. Ex. 40 | nil | 0 | G | 4 | 20 | 40 | ○ | F | X | X |
| Com. Ex. 41 | $MgCl_2$ | 4 | G | 4 | 20 | 40 | Δ | F | ◎ | ◎ |

| | Evaluation | | | | | | |
|---|---|---|---|---|---|---|---|
| | Cracking resistance | Tensile tear-resistance | Water resistance | Adhesiveness to container after heating | Re-adhesiveness to container | Transparency | Comprehensive evaluation |
| Com. Ex. 38 | X | ○ | X | X | X | ○ | X |
| Com. Ex. 39 | ○ | X | X | ○ | ○ | ○ | X |
| Com. Ex. 40 | X | ○ | X | X | X | ○ | X |
| Com. Ex. 41 | ○ | X | X | ○ | ○ | ○ | X |

As shown in Tables 2 to 7, it was found that the sheets each obtained from a dispersion liquid that has a composition of 1 to 5 mass % of a galactose-partial degradation product and 0.5 to 12 mass % of an inorganic compound ($MgCl_2$, $CaCl_2$, or $AlCl_3$) had water resistance and flexibility and are very excellent sheets. Meanwhile, the sheet including NaCl did not have flexibility. The tackiness of a sheet tended to become stronger by incorporating a relatively large amount of $MgCl_2$, $CaCl_2$, or $AlCl_3$ in the gel composition. Further, it was found that it is possible to produce a sheet while with its thickness adjustable by changing the input amount to the plastic dish.

When sheet production was attempted in the same manner as the aforementioned examples using galactoxyloglucan (manufactured by DSP GOKYO FOOD & CHEMICAL Co., Ltd., GLYLOID (registered trademark)) in which a galactose moiety is not removed, a sheet having flexibility was obtained from a gel composition including $MgCl_2$, but this sheet dissolved when it was immersed in water. Thus, it was found that the combination of the partial degradation product of the galactose moiety of the galactoxyloglucan and the inorganic compound (MgCl$_2$, CaCl$_2$, or AlCl$_3$) is necessary to impart water resistance and flexibility to the sheet.

Experimental Example 3

(1) Production of Gel Compositions of Examples 64 to 69

Gel compositions were produced in the same manner as Examples 1 to 4 except that the formulations as shown in Tables 8 to 10 below were employed, and evaluations were made in the same manner. The results are shown in Tables 8 to 10.

(2) Production of Gel Composition of Comparative Example 42

Gel compositions were produced in the same manner as Comparative Examples 4 to 40 except that the formulation as shown in Table 8 below was employed, and evaluations were made in the same manner. The results are shown in Table 8.

TABLE 8

|  | Inorganic salt, mass % |  | Polysaccharide, mass % |  | Input amount (g) | Temperature (° C.) | Composition type | Evaluation ||||| 
|---|---|---|---|---|---|---|---|---|---|---|---|---|
|  |  |  |  |  |  |  |  | Gel formation | Elasticity | Tensile tear-resistance | Water resistance | Comprehensive evaluation |
| Com. Ex. 42 | nil | 0 | part | 10 | 40 | 80 | G | ○ | Δ | X | ○ | Δ |
| Ex. 64 | MgCl$_2$ | 10 | part | 10 | 40 | 80 | G | ○ | ◎ | ○ | ○ | ◎ |

TABLE 9

|  | Inorganic salt, mass % |  | Polysaccharide, mass % |  | Input amount (g) | Temperature (° C.) | Composition type | Evaluation ||||| 
|---|---|---|---|---|---|---|---|---|---|---|---|---|
|  |  |  |  |  |  |  |  | Gel formation | Elasticity | Tensile tear-resistance | Water resistance | Comprehensive evaluation |
| Ex. 65 | MgCl$_2$ | 2 | part | 4 | 40 | 80 | G | ○ | ◎ | ○ | ○ | ◎ |
|  | CaCl$_2$ | 2 |  |  |  |  |  |  |  |  |  |  |
| Ex. 66 | MgCl$_2$ | 2 | part | 4 | 40 | 80 | G | ○ | ◎ | ○ | ○ | ◎ |
|  | AlCl$_3$ | 2 |  |  |  |  |  |  |  |  |  |  |
| Ex. 67 | CaCl$_2$ | 2 | part | 4 | 40 | 80 | G | ○ | ◎ | ○ | ○ | ◎ |
|  | AlCl$_3$ | 2 |  |  |  |  |  |  |  |  |  |  |
| Ex. 68 | MgCl$_2$ | 3.8 | part | 4 | 40 | 80 | G | ○ | ◎ | ○ | ○ | ◎ |
|  | NaCl | 0.2 |  |  |  |  |  |  |  |  |  |  |

TABLE 10

|  | Inorganic salt, mass % |  | Polysaccharide, mass % |  | Input amount (g) | Temperature (° C.) | Composition type | Evaluation ||||| 
|---|---|---|---|---|---|---|---|---|---|---|---|---|
|  |  |  |  |  |  |  |  | Gel formation | Elasticity | Tensile tear-resistance | Water resistance | Comprehensive evaluation |
| Ex. 69 | MgCl$_2$ | 2 | part | 10 | 40 | 80 | G | ○ | ◎ | ○ | ○ | ◎ |
|  | CaCl$_2$ | 1 |  |  |  |  |  |  |  |  |  |  |
|  | AlCl$_3$ | 1 |  |  |  |  |  |  |  |  |  |  |

Experimental Example 4

(1) Production of Sheets of Examples 70 to 86

Sheets were produced in the same manner as Examples 5 to 63 except that the formulations as shown in Tables 11 to 13 below were employed, and evaluations were made in the same manner. The results are shown in Tables 11 to 13.

(2) Production of Sheets of Reference Example 1 and Comparative Examples 43 to 45

Sheets were produced in the same manner as Comparative Examples 2 to 40 except that the formulation as shown in Table 14 below was employed, and evaluations were made in the same manner. The results are shown in Table 14.

TABLE 11

| | Inorganic salt, mass % | | Polysaccharide, mass % | | Input amount (g) | Temperature (° C.) | Evaluation | | | |
|---|---|---|---|---|---|---|---|---|---|---|
| | | | | | | | GSF formation | Sheet classification | Flexibility | Extensibility |
| Ex. 70 | CaCl$_2$ | 0.5 | part | 1 | 20 | 40 | ○ | F | ◎ | ◎ |
| Ex. 71 | CaCl$_2$ | 1 | part | 2 | 20 | 40 | ○ | F | ◎ | ◎ |
| Ex. 72 | CaCl$_2$ | 4 | part | 3 | 20 | 40 | ○ | F | ◎ | ◎ |
| Ex. 73 | CaCl$_2$ | 10 | part | 5 | 20 | 40 | ○ | GS | ◎ | ◎ |
| Ex. 74 | AlCl$_3$ | 0.5 | part | 1 | 20 | 40 | ○ | F | ◎ | ◎ |
| Ex. 75 | AlCl$_3$ | 1 | part | 2 | 20 | 40 | ○ | F | ◎ | ◎ |
| Ex. 76 | AlCl$_3$ | 4 | part | 3 | 20 | 40 | ○ | F | ◎ | ◎ |
| Ex. 77 | AlCl$_3$ | 10 | part | 5 | 20 | 40 | ○ | S | ○ | ○ |
| Ex. 78 | MgCl$_2$ | 10 | part | 10 | 20 | 40 | ○ | S | ◎ | ◎ |

| | Evaluation | | | | | | |
|---|---|---|---|---|---|---|---|
| | Cracking resistance | Tensile tear-resistance | Water resistance | Adhesiveness to container after heating | Re-adhesiveness to container | Transparency | Comprehensive evaluation |
| Ex. 70 | ○ | ○ | ○ | ○ | ○ | ○ | ◎ |
| Ex. 71 | ○ | ○ | ○ | ○ | ○ | ○ | ◎ |
| Ex. 72 | ○ | ○ | ○ | ○ | ○ | ○ | ◎ |
| Ex. 73 | ○ | ○ | ○ | ○ | ○ | ○ | ◎ |
| Ex. 74 | ○ | Δ | ○ | ○ | ○ | ○ | ◎ |
| Ex. 75 | ○ | Δ | ○ | ○ | ○ | ○ | ◎ |
| Ex. 76 | ○ | Δ | ○ | ○ | ○ | ○ | ◎ |
| Ex. 77 | Δ | Δ | ○ | ○ | ○ | X | ○ |
| Ex. 78 | ○ | ○ | ○ | ○ | ○ | ○ | ◎ |

TABLE 12

| | Inorganic salt, mass % | | Polysaccharide, mass % | | Input amount (g) | Temperature (° C.) | Evaluation | | | |
|---|---|---|---|---|---|---|---|---|---|---|
| | | | | | | | GSF formation | Sheet classification | Flexibility | Extensibility |
| Ex. 79 | MgCl$_2$<br>CaCl$_2$ | 2<br>2 | part | 4 | 20 | 40 | ○ | S | ◎ | ◎ |
| Ex. 80 | MgCl$_2$<br>AlCl$_3$ | 2<br>2 | part | 4 | 20 | 40 | ○ | S | ◎ | ◎ |
| Ex. 81 | CaCl$_2$<br>AlCl$_3$ | 2<br>2 | part | 4 | 20 | 40 | ○ | S | ◎ | ◎ |
| Ex. 82 | MgCl$_2$<br>NaCl | 3.8<br>0.2 | part | 4 | 20 | 40 | ○ | S | ◎ | ◎ |

| | Evaluation | | | | | | |
|---|---|---|---|---|---|---|---|
| | Cracking resistance | Tensile tear-resistance | Water resistance | Adhesiveness to container after heating | Re-adhesiveness to container | Transparency | Comprehensive evaluation |
| Ex. 79 | ○ | ○ | ○ | ○ | ○ | ○ | ◎ |
| Ex. 80 | ○ | ○ | ○ | ○ | ○ | ○ | ◎ |
| Ex. 81 | ○ | ○ | ○ | ○ | ○ | ○ | ◎ |
| Ex. 82 | ○ | ○ | ○ | ○ | ○ | ○ | ◎ |

TABLE 13

| | Inorganic salt, mass % | | Polysaccharide, mass % | | Input amount (g) | Temperature (° C.) | Evaluation | | | |
|---|---|---|---|---|---|---|---|---|---|---|
| | | | | | | | GSF formation | Sheet classification | Flexibility | Extensibility |
| Ex. 83 | MgCl$_2$ | 0.3 | part | 1 | 20 | 40 | ○ | F | ◎ | ◎ |
| | CaCl$_2$ | 0.1 | | | | | | | | |
| | AlCl$_3$ | 0.1 | | | | | | | | |
| Ex. 84 | MgCl$_2$ | 1 | part | 3 | 20 | 40 | ○ | F | ◎ | ◎ |
| | CaCl$_2$ | 1 | | | | | | | | |
| | AlCl$_3$ | 1 | | | | | | | | |
| Ex. 85 | MgCl$_2$ | 2 | part | 4 | 20 | 40 | ○ | S | ◎ | ◎ |
| | CaCl$_2$ | 1 | | | | | | | | |
| | AlCl$_3$ | 1 | | | | | | | | |
| Ex. 86 | MgCl$_2$ | 4 | part | 5 | 20 | 40 | ○ | GS | ◎ | ◎ |
| | CaCl$_2$ | 4 | | | | | | | | |
| | AlCl$_3$ | 2 | | | | | | | | |

| | Evaluation | | | | | | |
|---|---|---|---|---|---|---|---|
| | Cracking resistance | Tensile tear-resistance | Water resistance | Adhesiveness to container after heating | Re-adhesiveness to container | Transparency | Comprehensive evaluation |
| Ex. 83 | ○ | ○ | ○ | ○ | ○ | ○ | ◎ |
| Ex. 84 | ○ | ○ | ○ | ○ | ○ | ○ | ◎ |
| Ex. 85 | ○ | ○ | ○ | ○ | ○ | ○ | ◎ |
| Ex. 86 | ○ | ○ | ○ | ○ | ○ | ○ | ◎ |

TABLE 14

| | Inorganic salt, mass % | | Polysaccharide, mass % | | Input amount (g) | Temperature (° C.) | Evaluation | | | |
|---|---|---|---|---|---|---|---|---|---|---|
| | | | | | | | GSF formation | Sheet classification | Flexibility | Extensibility |
| Ref. Ex. 1 | NaCl | 0.5 | part | 1 | 20 | 40 | ○ | F | ○ | Δ |
| Com. Ex. 43 | NaCl | 1 | part | 2 | 20 | 40 | ○ | F | ○ | X |
| Com. Ex. 44 | NaCl | 4 | part | 3 | 20 | 40 | ○ | F | X | X |
| Com. Ex. 45 | NaCl | 10 | part | 5 | 20 | 40 | ○ | S | X | X |

| | Evaluation | | | | | | |
|---|---|---|---|---|---|---|---|
| | Cracking resistance | Tensile tear-resistance | Water resistance | Adhesiveness to container after heating | Re-adhesiveness to container | Transparency | Comprehensive evaluation |
| Ref. Ex. 1 | ○ | Δ | ○ | X | X | X | ○ |
| Com. Ex. 43 | ○ | Δ | ○ | X | X | X | X |
| Com. Ex. 44 | X | ○ | ○ | X | X | X | X |
| Com. Ex. 45 | X | ○ | ○ | X | X | X | X |

As shown in Table 8, a gel obtained from a dispersion liquid that has a composition of 10 mass % of a galactose-partial degradation product and 10 mass % of an inorganic compound (MgCl$_2$) had strength as well as elasticity, and was an excellent gel. As shown in Table 9 and Table 10, a gel obtained from a dispersion liquid that has a composition of two or three kinds of inorganic compounds (MgCl$_2$, CaCl$_2$, AlCl$_3$) also had strength as well as elasticity, and was an excellent gel.

As shown in Table 12 and Table 13, a sheet obtained from a dispersion liquid that has a composition of two or three kinds of inorganic compounds (MgCl$_2$, CaCl$_2$, AlCl$_3$) also had flexibility as well as water resistance, and was an excellent sheet. Even when 0.2 mass % of NaCl was included in a sheet that includes 3.8 mass % of MgCl$_2$, this sheet had flexibility as well as water resistance, and was an excellent sheet.

As shown in Table 11, a sheet obtained from a dispersion liquid that has a composition of 1 to 5 mass % of a galactose-partial degradation product and 0.5 to 10 mass % of inorganic compounds (CaCl$_2$, AlCl$_3$) had flexibility as well as water resistance, and was an excellent sheet. A sheet obtained from a dispersion liquid that has a composition of 10 mass % of a galactose-partial degradation product and 10 mass % of an inorganic compound (MgCl$_2$) also had flexibility as well as water resistance, and was an excellent sheet. Meanwhile, as shown in Table 14, a sheet including 2 to 5 mass % of a galactose-partial degradation product and 1 to 10 mass % of NaCl did not have flexibility, while a sheet including 1 mass % of a galactose-partial degradation product and 0.5 mass % of NaCl had flexibility as well as water resistance.

Experimental Example 5

Stability of Sheet Including Inorganic Compound as the Aforementioned Compound

Sheets including magnesium chloride and calcium chloride were produced in the same manner as Examples 39 and 40, and allowed to stand still at 50° C. for 1 month. After left standing for 1 month, the sheets were moved to a room temperature environment and allowed to stand still at room temperature for 1 day or more. After left standing, evaluation was made on flexibility, extensibility, and water resistance in the manner mentioned above. Both of the sheets that were allowed to stand still at 50° C. for 1 month showed flexibility, extensibility and water resistance comparable to those of the sheet obtained in Experimental Example 2 (Examples 39 and 40).

Experimental Example 6

Sheet Physical Property Evaluation

The breaking strains of the sheets of Examples 39, 40 and 41 produced in Experimental Example 2 (sheets including 4 mass % of magnesium chloride, calcium chloride or aluminum chloride, and 4 mass % of a galactose-partial degradation product) and the sheet of Comparative Example 26 were measured according to JIS K7127 (1999) except that the tension rate of 60 mm/min was employed. The results are shown in Table 15. As shown in Table 15, the sheets obtained by adding various inorganic compounds exhibited a breaking strain much larger than that of the sheet containing no inorganic compound (inorganic compound free). Accordingly, it was found that the sheets obtained by adding various inorganic compounds have excellent ductility.

TABLE 15

|  | Inorganic compound | Breaking strain (%) |
| --- | --- | --- |
| Com. Ex. 26 | nil | 1.0 |
| Ex. 39 | $MgCl_2$ | 63.5 |
| Ex. 40 | $CaCl_2$ | 46.4 |
| Ex. 41 | $AlCl_3$ | 25.8 |

Although the reason why the sheets of Examples are excellent in flexibility, strength and additionally extensibility is uncertain, it is assumed that hydration occurs when a galactose-partial degradation product takes in an inorganic compound, and this hydrated water contributes to the flexibility of a sheet after drying. Specifically, it is assumed that such excellent properties are produced by strengthening of intermolecular bond due to intercalation of inorganic salt (ion) into a gel (molecules of a partial-degradation product) and increase of hydrated water content due to taking-in of an inorganic compound (inorganic salt). Since galactoxyloglucan that acts as a basic structure of the galactose-partial degradation product is neutral polysaccharide, it is assumed that the gelation mechanism is different from a gelation mechanism by crosslinking between carboxyl groups with ions (Ca, Mg, etc.) which can be seen in pectin or the like.

The sheet of each Example immediately after heating and drying seemingly has little water and low flexibility in some case. However, it was found that the water content of the sheet comes to equilibrium when stored in a room for several days, and thereby the sheet can obtain flexibility.

In the sheet of each Example, the range of the amount of an inorganic salt to be added, which enables to produce a better sheet, tended to slightly vary according to the concentration of the partial degradation product. The upper limit of the inorganic salt content, which enables to produce a better sheet, also tended to be higher as the concentration of the partial degradation product increases.

In view of these tendencies, the ratio between the galactose-partial degradation product and the inorganic compound is preferably 4:1 to 1:3, more preferably 3:1 to 1:1.5, although it varies depending on the amount of the galactose-partial degradation product added as mentioned above.

Specifically, the content of magnesium chloride is preferably 0.5 to 1 mass % when the content of the galactose-partial degradation product is 1 to 2 mass %; the content of magnesium chloride is preferably 1 to 4 mass % when the content of the galactose-partial degradation product is 3 to 4 mass %; and the content of magnesium chloride is preferably 2 to 10 mass % when the content of the galactose-partial degradation product is 5 mass %. The content of magnesium chloride is preferably 5 to 10 mass % when the content of the galactose-partial degradation product is more than 5 mass % and 10 mass % or less. This result suggested that the higher the concentration of the galactose-partial degradation product, the higher the likelihood that a gel (network) structure can take in more inorganic salt.

It was found that, when the content of the inorganic salt is an optimum amount or lower, a sheet having poor flexibility and strength is produced, and, when the content of the inorganic salt is beyond the optimum amount, a gel is hardly formed due to the increase in the content of the inorganic salt, and the obtained product turns to be a product having an intermediate viscosity between a gelled product and a highly viscous product, or turns to be simply a highly viscous product. According to such characteristic features of the inorganic salt, it was found that a sheet having tackiness (being excellent in tackiness) can be produced by adding the inorganic salt in an amount equal to or lower than the excessive amount and a relatively large amount.

Experimental Example 7

Gel compositions were produced in the same manner as Examples 1 to 4 except that the formulation as shown in Table 16 below was employed, and evaluation was made in the same manner as mentioned above. The results are shown in Table 16. The results of Comparative Example 1 and Example 1 in Table 1 are shown together in Table 16.

TABLE 16

|  | Inorganic salt, mass % |  | Polysaccharide, mass % |  | Input amount (g) | Temperature (° C.) | Composition type | Evaluation |  |  |  |  |
| --- | --- | --- | --- | --- | --- | --- | --- | --- | --- | --- | --- | --- |
|  |  |  |  |  |  |  |  | Gel formation | Elasticity | Tensile tear-resistance | Water resistance | Comprehensive evaluation |
| Com. Ex. 1 | nil |  | partial degradation product | 0 | 4 | 40 | 80 | gel | ○ | Δ | X | ○ | Δ |
| Ex. 1 | $MgCl_2$ | 4 | partial degradation product | 4 | 4 | 40 | 80 | gel | ○ | ◎ | ○ | ○ | ◎ |

TABLE 16-continued

| | Inorganic salt, mass % | | Polysaccharide, mass % | | Input amount (g) | Temperature (° C.) | Composition type | Evaluation | | | | |
|---|---|---|---|---|---|---|---|---|---|---|---|---|
| | | | | | | | | Gel formation | Elasticity | Tensile tear-resistance | Water resistance | Comprehensive evaluation |
| Ex. 87 | MAP | 4 | partial degradation product | 4 | 40 | 80 | gel | ○ | ◎ | ○ | ○ | ◎ |
| Ex. 88 | NAP | 4 | partial degradation product | 4 | 40 | 80 | gel | ○ | ◎ | ○ | ○ | ◎ |
| Ex. 89 | MgG | 4 | partial degradation product | 4 | 40 | 80 | gel | ○ | ◎ | ○ | ○ | ◎ |
| Ex. 90 | CaG | 4 | partial degradation product | 4 | 40 | 80 | gel | ○ | ◎ | ○ | ○ | ◎ |
| Ex. 91 | CaP | 4 | partial degradation product | 4 | 40 | 80 | gel | ○ | ◎ | ○ | ○ | ◎ |
| Ex. 92 | AlMgSil | 4 | partial degradation product | 4 | 40 | 80 | gel | ○ | ○ | Δ | ○ | ○ |
| Ex. 93 | MgBr$_2$ | 4 | partial degradation product | 4 | 40 | 80 | gel | ○ | ○ | Δ | ○ | ○ |
| Ex. 94 | MgOAc$_2$ | 4 | partial degradation product | 4 | 40 | 80 | gel | ○ | ◎ | ○ | ○ | ◎ |
| Ex. 95 | Na$_2$SO$_4$ | 4 | partial degradation product | 4 | 40 | 80 | gel | ○ | ◎ | ○ | ○ | ◎ |

As shown in Table 16, it was found that gel compositions each obtained by mixing 4 mass % of the aforementioned compound and 4 mass % of the galactose-partial degradation product have high elasticity and strength, for example, in a case where an organic compound (organic salt) such as magnesium ascorbyl phosphate (MAP), sodium ascorbyl phosphate (NAP), magnesium gluconate (MgG), calcium gluconate (CaG), calcium pantothenate (CaP), and magnesium acetate (MgOAc$_2$) is used as the aforementioned compound, and an inorganic compound (inorganic salt) such as magnesium aluminum silicate (AlMgSil), magnesium bromide (MgBr$_2$), and sodium sulfate (Na$_2$SO$_4$) is used as the aforementioned compound. Thus, it was found that these gel compositions exhibit excellent gel characteristics.

Experimental Example 8

Sheets were produced in the same manner as Examples 1 to 4 except that the formulation as shown in Table 17 below was employed, and evaluation was made in the same manner as mentioned above. The results are shown in Table 17. The results of Comparative Example 25 in Table 4 and the results of Example 38 in Table 5 are shown together in Table 17.

TABLE 17

| | Inorganic salt, mass % | Polysaccharide, mass % | Input amount (g) | Temperature (° C.) | Evaluation | | | |
|---|---|---|---|---|---|---|---|---|
| | | | | | GSF formation | Sheet classification | Flexibility | Extensibility |
| Com. Ex. 25 | nil | 0 | part | 4 | 20 | 80 | ○ | S | X | X |
| Ex. 38 | MgCl$_2$ | 4 | part | 4 | 20 | 80 | ○ | S | ◎ | ◎ |
| Com. Ex. 46 | MAP | 4 | part | 4 | 20 | 80 | ○ | S | X | X |
| Com. Ex. 47 | NAP | 4 | part | 4 | 20 | 80 | ○ | S | X | X |
| Com. Ex. 48 | MgG | 4 | part | 4 | 20 | 50 | ○ | S | X | X |
| Com. Ex. 49 | CaG | 4 | part | 4 | 20 | 80 | ○ | S | X | X |
| Com. Ex. 50 | CaP | 4 | part | 4 | 20 | 80 | ○ | S | X | X |
| Com. Ex. 51 | NAP | 4 | part | 4 | 20 | 40 | ○ | S | X | X |
| Com. Ex. 52 | CAP | 4 | part | 4 | 20 | 40 | ○ | S | X | X |
| Ex. 96 | MgBr$_2$ | 4 | part | 4 | 20 | 40 | ○ | S | ◎ | ○ |
| Com. Ex. 53 | Na$_2$SO$_4$ | 4 | part | 4 | 20 | 40 | ○ | S | ◎ | X |

| | Evaluation | | | | | | |
|---|---|---|---|---|---|---|---|
| | Cracking resistance | Tensile tear-resistance | Water resistance | Adhesiveness to container after heating | Re-adhesiveness to container | Transparency | Comprehensive evaluation |
| Com. Ex. 25 | X | ○ | ○ | X | X | ○ | X |
| Ex. 38 | ○ | ○ | ○ | ○ | ○ | ○ | ◎ |

TABLE 17-continued

| | | | | | | | |
|---|---|---|---|---|---|---|---|
| Com. Ex. 46 | X | ○ | ○ | X | X | ○ | X |
| Com. Ex. 47 | Δ | ○ | ○ | ○ | X | ○ | X |
| Com. Ex. 48 | X | ○ | ○ | ○ | X | Δ | X |
| Com. Ex. 49 | X | ○ | ○ | ○ | X | X | X |
| Com. Ex. 50 | X | ○ | ○ | ○ | X | X | X |
| Com. Ex. 51 | X | ○ | ○ | ○ | X | ○ | X |
| Com. Ex. 52 | X | ○ | ○ | ○ | X | ○ | X |
| Ex. 96 | ○ | ○ | ○ | ○ | ○ | ○ | ◎ |
| Com. Ex. 53 | X | X | ○ | ○ | X | X | X |

As shown in Table 17, it was found that when magnesium bromide among the compounds shown in Table 16 is used, a sheet obtained by mixing 4 mass % of magnesium bromide and 4 mass % of a galactose-partial degradation product has water resistance and flexibility. Thus, it was found that this sheet exhibits excellent sheet characteristics. It was found that even when any one of the compounds shown in Table 16 is used, an obtained sheet has water resistance.

It was found from the above that a sheet can be imparted with very high flexibility and extensibility when the sheet includes an inorganic salt of magnesium, calcium or aluminum, especially a chloride salt along with a galactose-partial degradation product.

Meanwhile, it was found that a sheet cannot be imparted with flexibility and extensibility when the sheet includes even an organic salt of magnesium, calcium or aluminum along with a galactose-partial degradation product. It was also found that when a sheet includes ascorbyl phosphate salt along with a galactose-partial degradation product, the sheet cannot be imparted with flexibility and extensibility as mentioned above, but can be imparted with transparency, unlike gluconate or pantothenate. It is assumed that this result was caused because a galactose-partial degradation product has affinity to ascorbyl phosphate salt (that is, a galactose-partial degradation product has properties to include ascorbyl phosphate salt, i.e., inclusivity) even after drying, while a sheet including both components has low hydration properties (water absorbability).

Further, a sheet of any of Comparative Examples, which was once dried at the time of production, was not imparted with flexibility and extensibility, even if the sheet was made to absorb moisture thereafter. It is assumed that this result was caused because a sheet has low hydration properties (water absorbability) even if the sheet includes a galactose-partial degradation product along with the compound of any of Comparative Examples.

A sheet can be forcibly made to absorb water by, after drying the sheet, making the sheet absorb water through moisture in the external environment to allow the sheet to contain water, or adding an aqueous solvent to the sheet. Examples of the method for adding an aqueous solvent to a sheet after drying include, for example, applying an aqueous solvent onto the sheet, and immersing the sheet in an aqueous solvent. A sheet which has been produced by drying a gel composition releases water contained itself or absorbs water in the environment, so that the sheet contains a certain amount of water when the time elapses (steady state). Accordingly, when a sheet has been excessively dried to have a water content lower than that in the steady state, the sheet can be made to absorb water until the water content of the sheet returns to the level in the steady state. In this case, a sheet imparted with flexibility and extensibility can be obtained when a compound enabling a dried sheet after drying to have a relatively high water absorbability is used, that is, when a sheet including an inorganic compound is used.

Experimental Example 9

For the compounds, namely magnesium salt, calcium salt, aluminum salt, and sodium salt to be included in a sheet along with a galactose-partial degradation product, the relationship between the hydrated water and solubility of the compounds and the flexibility and extensibility of the sheets including these compounds was investigated. The results are shown in Table 18.

TABLE 18

| | Salt compound | Hydration water | Solubility of salt compound (g/100 mL) Dissolution temperature | | Evaluation | |
|---|---|---|---|---|---|---|
| | | | 20° C. | 30° C. | Flexibility | Extensibility |
| Com. Ex. 25 | nil | 0 | — | — | X | X |
| Ex. 38 | $MgCl_2$ | hexahydrate | 54.6 | 55.8 | ◎ | ◎ |
| Com. Ex. 49 | CaG (Ca gluconate) | monohydrate | 3.3 (25° C.) | — | X | X |
| Com. Ex. 50 Com. Ex. 52 | CaP (Ca pantothenate) | monohydrate | 5 (25° C.) | — | X | X |
| Ex. 96 | $MgBr_2$ | hexahydrate | 101 | 104 | ◎ | ○ |
| Com. Ex. 53 | $Na_2SO_4$ | anhydrous | 19.5 | 40.8 | X | X |

As shown in Table 18, it was found that a sheet generally tends to have increased flexibility and extensibility, as the hydrated water of the added compound or the solubility of the added compound to water is increased. From this, it is assumed that the saturated water content of a sheet, which may influence on the flexibility and extensibility of the sheet, as mentioned above, may also influence on the hydration properties (water absorbability) of an inorganic compound present in the sheet, the affinity between the galactose-partial degradation product and the inorganic compound, or the affinity between the galactose-partial degradation product and water combined with the inorganic compound. From the above, it was found that an inorganic compound excellent in hydration properties and affinity is preferable as an inorganic compound that is to be included in the sheet along with a galactose-partial degradation product and that is one kind or two or more kinds selected from the group consisting of magnesium salt, calcium salt and aluminum salt. As the index of the hydration properties, the number of molecules of hydrated water and the solubility of the inorganic compound to water at 20° C. can be mentioned, and the number of molecules of the hydrated water of the compound is preferably 2 to 10, and the solubility to water at 20° C. is preferably 20 to 100 g/100 mL.

Experimental Example 10

Production of Gel Face Pack 1

16.0 g (4 mass %) of a galactose-partial degradation product was added to a metal container with a width of 25 cm and a length of 30 cm, then 16.0 g (4 mass %) of $MgCl_2$ was added thereto, and then water at room temperature was added thereto to amount to 400 g in total, followed by stirring with a plastic stirrer (about 30 seconds) to obtain a dispersion liquid including the galactose-partial degradation product and $MgCl_2$. The metal container with the obtained dispersion liquid kept therein was placed in a freezer [manufactured by HOSHIZAKI ELECTRIC CO., LTD.; model: HRF-180XF] set at −20° C. and held in this state for 2 hours so that it was cooled to −20° C., and thereafter, it was thawed at room temperature. After thawing, it was heated at 80° C. for 2 hours using a thermostatic device [manufactured by ESPEC CORP., model type: PR-2KP] to produce a gel composition. After heating, the gel composition was allowed to stand still at room temperature so that it was cooled to room temperature. The obtained gel composition was cut into a face shape to produce a gel face pack. The obtained gel face pack exhibited high elasticity and strength. The gel face pack also exhibited an appropriate degree of extensibility and was also excellent in adhesiveness.

Production of Gel Face Pack 2

16.0 g (4 mass %) of a galactose-partial degradation product was added to a metal container with a width of 25 cm and a length of 30 cm, then 16.0 g (4 mass %) of magnesium ascorbyl phosphate was added thereto, and then water at room temperature was added thereto to amount to 400 g in total, followed by stirring with a plastic stirrer (about 30 seconds) to produce a dispersion liquid including the galactose-partial degradation product and magnesium ascorbyl phosphate. The metal container with the obtained dispersion liquid kept therein was placed in a freezer [manufactured by HOSHIZAKI ELECTRIC CO., LTD.; model: HRF-180XF] set at −20° C. and held in this state for 2 hours so that it was cooled to −20° C., and thereafter, it was thawed at room temperature. After thawing, it was heated at 35° C. for 4 hours using a thermostatic device [manufactured by ESPEC CORP., model type: PR-2KP]. After heating, the gel composition was allowed to stand still at room temperature so that it was cooled to room temperature. The obtained gel composition was cut into a face shape to produce a gel face pack. The obtained gel face pack exhibited high elasticity and strength in the same manner as the gel face pack including $MgCl_2$. The gel face pack also exhibited an appropriate degree of extensibility and was also excellent in adhesiveness.

When the aforementioned gel composition is dried by heating to locally reduce water on the surface side, the inner side of the gel composition tends to have elasticity and become relatively soft, while the surface side tends to become relatively hard while having flexibility. It is thus also possible to impart certain characteristics to the surface side, which are different from the characteristics of the inner side by adjusting the water content on the surface side.

The invention claimed is:

1. A gel composition comprising a partial degradation product of the galactose moiety of galactoxyloglucan, a compound, and an aqueous solvent,
    wherein the compound is one kind or two or more kinds selected from the group consisting of magnesium salt, calcium salt, aluminum salt and sodium salt, and
    wherein sodium salt is sodium ascorbyl phosphate or sodium sulfate.

2. The gel composition according to claim 1,
    wherein the content of the galactose-partial degradation product is 1 to 5 mass % based on the total mass of the gel composition.

3. The gel composition according to claim 1, wherein the content of the compound is 0.1 to 12 mass % based on the total mass of the gel composition.

4. A face pack comprising the gel composition according to claim 1.

5. A sheet comprising a partial degradation product of the galactose moiety of galactoxyloglucan, an inorganic compound, and an aqueous solvent,
    wherein the inorganic compound is one kind or two or more kinds selected from the group consisting of magnesium salt, calcium salt and aluminum salt.

6. The sheet according to claim 5, wherein the inorganic compound further comprises sodium salt or potassium salt.

7. The sheet according to claim 5, wherein the water content of the sheet is 10 to 35 mass % based on the total mass of the sheet.

8. A production method for a sheet according to claim 5, comprising the steps of:
    (1) mixing at room temperature the partial degradation product of the galactose moiety of galactoxyloglucan, the inorganic compound, and the aqueous solvent to obtain a mixture;
    (2) cooling or freezing the mixture obtained in step (1);
    (3) gelling the mixture cooled or frozen in step (2) by heating to obtain a gel composition that includes the galactose-partial degradation product, the inorganic compound, and the aqueous solvent; and
    (4) drying the gel composition produced in step (3) to produce a sheet.

9. The production method for the sheet according to claim 8, wherein the compound further comprises potassium salt.

10. The production method for the sheet according to claim 8,
    wherein, in step (1), the galactose-partial degradation product, the inorganic compound, and the aqueous solvent are mixed at 18 to 30° C.

11. The production method for the sheet according to claim 8,
    wherein, in step (1), the galactose-partial degradation product is mixed with the aqueous solvent and thereafter further mixed with the inorganic compound.

* * * * *